(12) United States Patent
Nakahara et al.

(10) Patent No.: US 12,013,640 B2
(45) Date of Patent: Jun. 18, 2024

(54) RESIST UNDERLAYER FILM MATERIAL, PATTERNING PROCESS, AND METHOD FOR FORMING RESIST UNDERLAYER FILM

(71) Applicant: SHIN-ETSU CHEMICAL CO., LTD., Tokyo (JP)

(72) Inventors: Takayoshi Nakahara, Joetsu (JP); Takeru Watanabe, Joetsu (JP); Daisuke Kori, Joetsu (JP); Yusuke Biyajima, Joetsu (JP); Tsutomu Ogihara, Joetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 488 days.

(21) Appl. No.: 17/329,767

(22) Filed: May 25, 2021

(65) Prior Publication Data

US 2021/0397092 A1    Dec. 23, 2021

(30) Foreign Application Priority Data

Jun. 12, 2020   (JP) ................................ 2020-102117

(51) Int. Cl.
*G03F 7/11* (2006.01)
*C07C 233/18* (2006.01)
(Continued)

(52) U.S. Cl.
CPC .............. *G03F 7/11* (2013.01); *C07C 233/18* (2013.01); *C07C 233/47* (2013.01);
(Continued)

(58) Field of Classification Search
None
See application file for complete search history.

(56) References Cited

U.S. PATENT DOCUMENTS 7,094,708 B2    8/2006  Kato et al.
2002/0106909 A1   8/2002  Kato et al.
(Continued)

FOREIGN PATENT DOCUMENTS

EP        3584238 A1 * 12/2019  ........... C07C 13/567
JP     2002-334869 A    11/2002
(Continued)

OTHER PUBLICATIONS

Nov. 8, 2021 Search Report issued in European Patent Application No. 21178062.2.

(Continued)

*Primary Examiner* — Martin J Angebranndt
(74) *Attorney, Agent, or Firm* — Oliff PLC

(57) ABSTRACT

A resist underlayer film material used in multilayer resist method contains (A) compound shown by following general formula (1), and (B) organic solvent, where X independently represents monovalent organic group shown by following general formula (2); W contains an "m" number of partial structures each independently shown by following formula (3); "m" and "n" each represent an integer of 1 to 10; broken lines represent bonding arms; Z represents aromatic group; A represents single bond or $-O-(CH_2)_p-$; "k" represents integer of 1 to 5; "p" represents integer of 1 to 10; $R^{01}$ represents hydrogen atom or monovalent organic group having 1 to 10 carbon atoms. Material is capable of forming resist underlayer film excellent in planarizing property in fine patterning process by multilayer resist method in semiconductor-device manufacturing process; and patterning processes and methods for forming resist underlayer film use material.

(Continued)

(J)

(K)

US 12,013,640 B2
Page 2

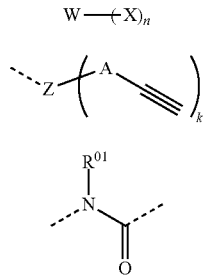

(1)
(2)
(3)

19 Claims, 3 Drawing Sheets

(51) Int. Cl.
C07C 233/47 (2006.01)
C07C 233/55 (2006.01)
C07D 251/34 (2006.01)
C07D 487/04 (2006.01)
C08F 38/00 (2006.01)
C09D 149/00 (2006.01)
G03F 7/09 (2006.01)

(52) U.S. Cl.
CPC .......... *C07C 233/55* (2013.01); *C07D 251/34* (2013.01); *C07D 487/04* (2013.01); *C08F 38/00* (2013.01); *C09D 149/00* (2013.01); *G03F 7/094* (2013.01); *C07C 2603/18* (2017.05)

(56) References Cited

U.S. PATENT DOCUMENTS

| | | |
|---|---|---|
| 2009/0274978 A1 | 11/2009 | Ohashi et al. |
| 2013/0302990 A1 | 11/2013 | Watanabe et al. |
| 2017/0183531 A1 | 6/2017 | Kori et al. |
| 2018/0011405 A1 | 1/2018 | Watanabe et al. |
| 2018/0158674 A1* | 6/2018 | Yamada .............. H01L 21/0276 |
| 2019/0300498 A1 | 10/2019 | Tachibana et al. |
| 2020/0333709 A1* | 10/2020 | Kori ................... H01L 21/31058 |
| 2022/0163890 A1* | 5/2022 | Kori ........................ G03F 7/162 |

FOREIGN PATENT DOCUMENTS

| | | | |
|---|---|---|---|
| JP | 2004-205685 A | 7/2004 | |
| JP | 2007-199653 A | 8/2007 | |
| JP | 2009-269953 A | 11/2009 | |
| JP | 2013-253227 A | 12/2013 | |
| JP | 2017-119670 A | 7/2017 | |
| JP | 2018-13768 A | 1/2018 | |
| WO | 2004/066377 A1 | 8/2004 | |
| WO | WO-2013024778 A1 * | 2/2013 | ............. C07C 37/20 |
| WO | WO-2020138147 A1 * | 7/2020 | ........... C07D 311/78 |

OTHER PUBLICATIONS

Apr. 25, 2023 Office Action Issued in Japanese Patent Application No. 2020-102117.

* cited by examiner

[FIG. 1]
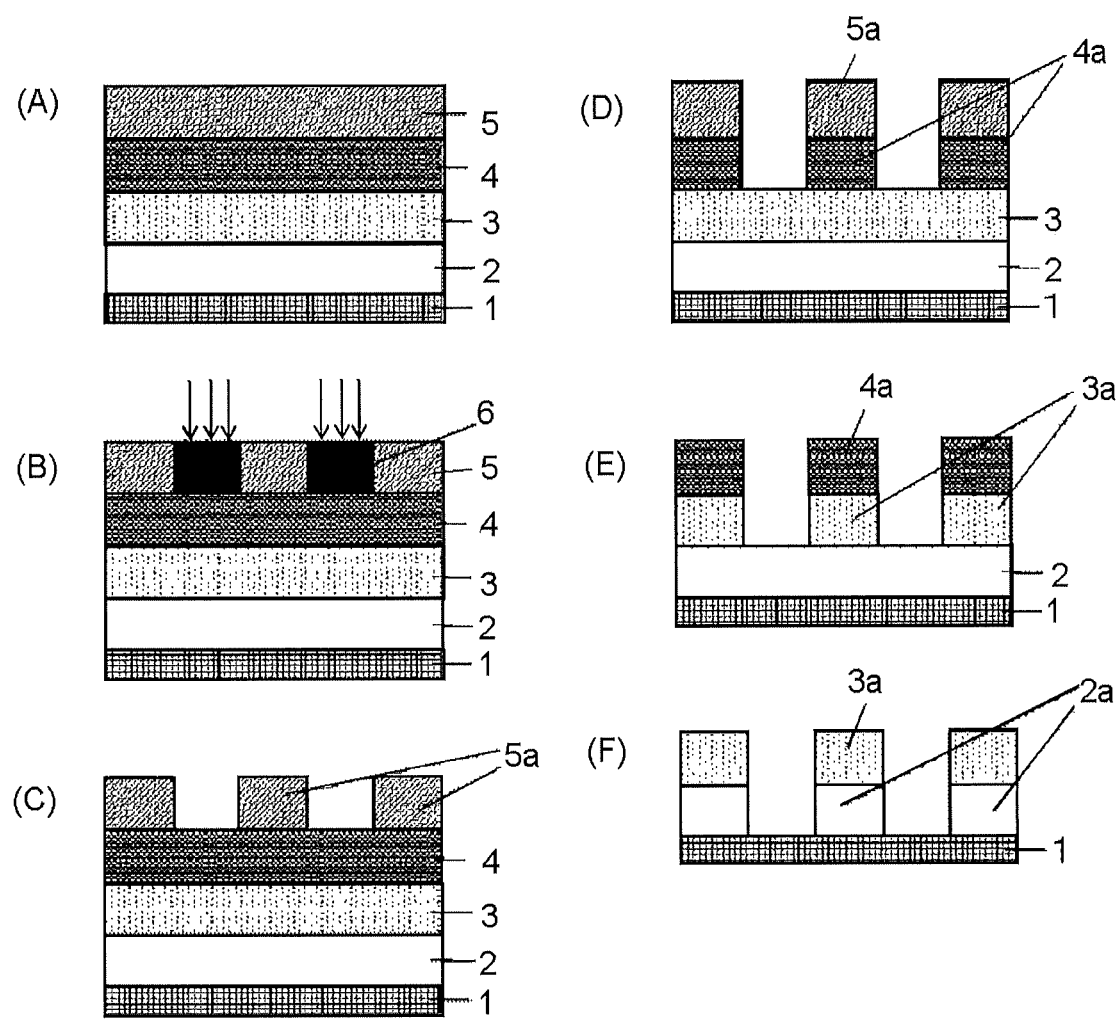

[FIG. 2]
(G)
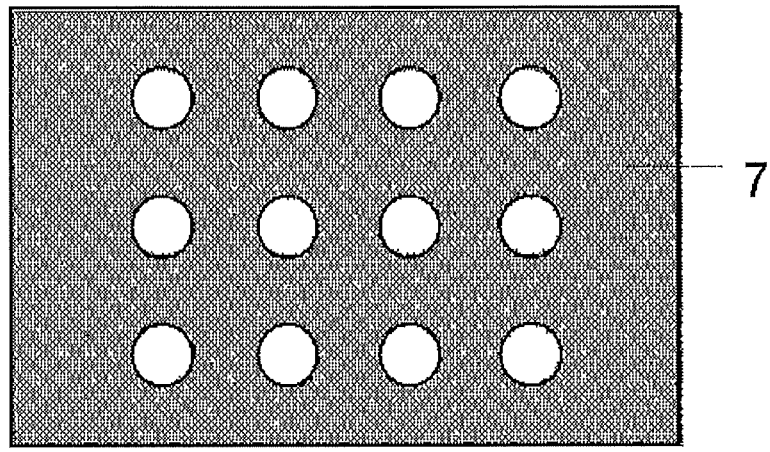
(H)
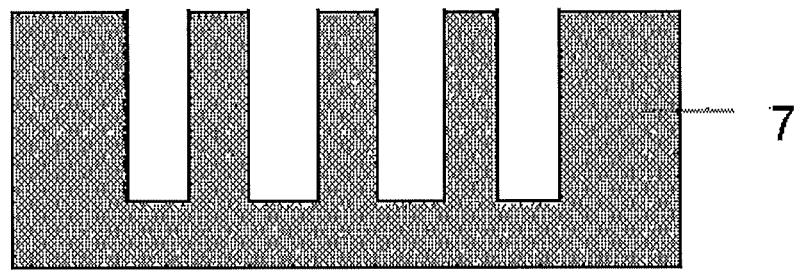
(I)
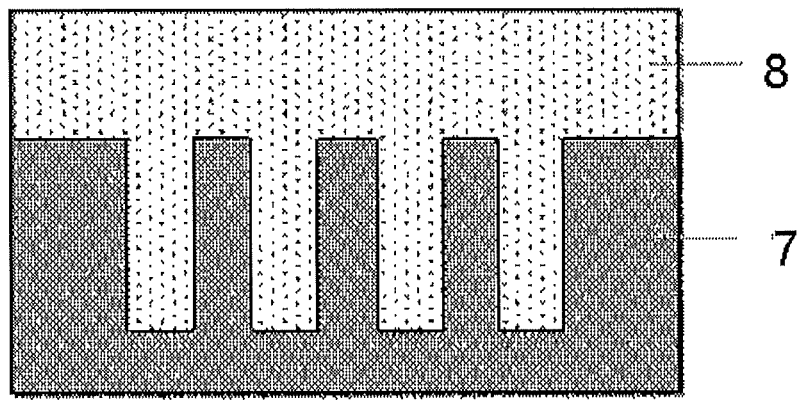

[FIG. 3]
(J)
(K)
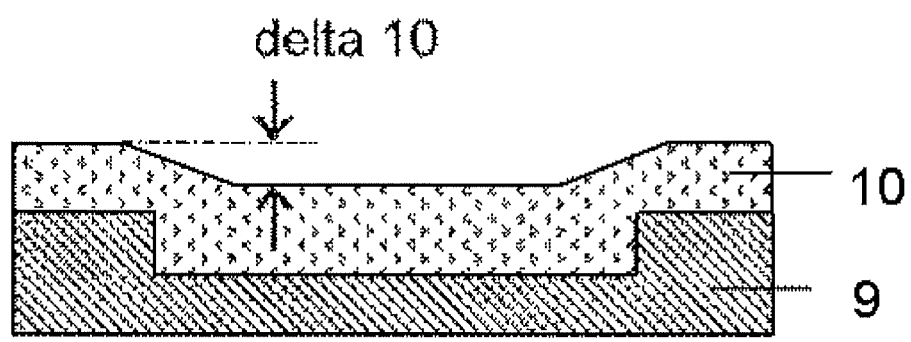

RESIST UNDERLAYER FILM MATERIAL, PATTERNING PROCESS, AND METHOD FOR FORMING RESIST UNDERLAYER FILM

TECHNICAL FIELD

The present invention relates to: a resist underlayer film material used for fine patterning by a multilayer resist method in a semiconductor-device manufacturing process; and a patterning process and a method for forming a resist underlayer film which use the material.

BACKGROUND ART

As LSI advances toward high integration and high processing speed, miniaturization of pattern size is progressing rapidly. Along with this miniaturization, lithography technology has achieved fine patterning by shortening the wavelength of a light source and selecting an appropriate resist composition accordingly. The composition mainly used is a positive photoresist composition for monolayer. The monolayer positive photoresist composition not only allows a resist resin to have a skeleton having etching resistance against dry etching with chlorine- or fluorine-based gas plasma, but also provides a switching mechanism that makes an exposed part soluble. Thereby, a pattern is formed by dissolving the exposed part, and the remaining resist pattern is used as an etching mask to process a substrate to be processed by dry etching.

However, when the pattern becomes finer, that is, the pattern width is reduced without changing the thickness of the photoresist film to be used, resolution performance of the photoresist film is lowered. In addition, pattern development of the photoresist film with a developer excessively increases what is called an aspect ratio of the pattern, resulting in pattern collapse problem. Therefore, photoresist films have been thinned along with the pattern miniaturization.

On the other hand, a substrate to be processed has been generally processed by dry etching using a pattern-formed photoresist film as an etching mask. In practice, however, there is no dry etching method capable of providing an absolute etching selectivity between the photoresist film and the substrate to be processed. Hence, there are problems that the resist film is damaged and collapses during processing of the substrate, and that the resist pattern cannot be precisely transferred to the substrate to be processed. Accordingly, higher dry etching resistance has been required in a resist composition along with the pattern miniaturization. Meanwhile, to enhance the resolution, resins used for photoresist compositions have been required to have low absorbance at the exposure wavelength. Accordingly, as the exposure light shifts to shorter wavelengths from i-beam to KrF and to ArF, the resin shifts to novolak resins, polyhydroxystyrene, and resins having aliphatic polycyclic skeletons. This shift actually accelerates an etching rate under dry etching conditions in processing the substrate, and recent photoresist compositions having high resolution tend to have low etching resistance.

As a result, a substrate to be processed has to be dry etched with a thinner photoresist film having lower etching resistance. It is important to establish a material and procedure for this processing.

A multilayer resist method is one solution for these problems. This method is as follows: a middle layer film having a different etching selectivity from a photoresist film (i.e., a resist upper layer film) is placed between the resist upper layer film and a substrate to be processed; a pattern is formed in the resist upper layer film; then, the pattern is transferred to the middle layer film by dry etching while using the resist upper layer film pattern as a dry etching mask; and the pattern is further transferred to the substrate to be processed by dry etching while using the middle layer film as a dry etching mask.

One of the multilayer resist methods is a three-layer resist method, which can be performed with a typical resist composition used in the monolayer resist method. This three-layer resist method includes, for example, the following steps: an organic film made of a novolak resin or the like is formed as a resist underlayer film on a substrate to be processed; a silicon-containing film is formed as a resist middle layer film on the resist underlayer film; a usual organic photoresist film is formed as a resist upper layer film on the resist middle layer film. Since the organic resist upper layer film exhibits a favorable etching selectivity ratio relative to the silicon-containing resist middle layer film when dry etching is performed with fluorine-based gas plasma, the resist upper layer film pattern can be transferred to the silicon-containing resist middle layer film by employing dry etching with fluorine-based gas plasma. According to this method, even if a resist composition to be used has difficulty in forming a pattern with a sufficient film thickness for directly processing the substrate to be processed or has insufficient dry etching resistance for processing the substrate, the pattern can be transferred to the silicon-containing film (resist middle layer film). Moreover, the subsequent dry etching with oxygen-based or hydrogen-based gas plasma enables the pattern to be transferred into the organic film (resist underlayer film) made of a novolak resin or the like having a sufficient dry etching resistance for processing the substrate. Numerous resist underlayer films as described above have been already known and disclosed in, for example, Patent Document 1, etc.

On the other hand, in recent years, semiconductor devices having novel structures, such as multi-gate structure, have been actively manufactured and studied. Accordingly, there are growing needs for a resist underlayer film having more excellent planarizing and filling properties than conventional ones. For example, when a substrate to be processed used as a base has a fine pattern structure, such as holes, trenches, and fins, gap-filling property is required to fill the gaps of the pattern with a resist underlayer film without voids. In addition, when the underlying substrate to be processed has a step(s) or when both a pattern-dense portion and a no-pattern region exist in one wafer, the film surface needs to be planarized (planarization) by a resist underlayer film. By planarizing the surface of the underlayer film, fluctuation in film thickness of a resist middle layer film and a resist upper layer film formed thereon can be controlled, and the reduction of a focus margin in lithography or margin in a subsequent step of processing the substrate to be processed can be controlled.

Moreover, the organic film material excellent in filling property and planarizing property is not limited to use for the underlayer film for multilayer resist, and is also widely usable as a planarizing material for manufacturing a semiconductor device, e.g., for planarizing a substrate prior to patterning by nanoimprinting, etc. Further, for global planarization in a semiconductor device manufacturing process, a CMP process is now generally used. However, the CMP process is costly, so that this material is also expected to be used for the global planarizing method, instead of CMP.

To form a planarizing film for planarizing an uneven semiconductor substrate, there is proposed a resist underlayer film material that contains a compound with a certain structure containing linear ether moieties and aromatic moieties having triple bonds at terminals (Patent Document 2). However, this material does not exhibit sufficient planarizing performance on a trench portion in a substrate, and does not satisfy needs in cutting-edge devices. There have been demands for a resist underlayer film material having excellent planarizing property on a variety of substrate structures.

CITATION LIST

Patent Literature

Patent Document 1: JP 2004-205685 A
Patent Document 2: JP 2017-119670 A

SUMMARY OF INVENTION

Technical Problem

The present invention has been made in view of the above circumstances. An object of the present invention is to provide: a resist underlayer film material having appropriate etching and optical properties and being capable of forming a resist underlayer film excellent in planarizing property even when a substrate to be processed has a portion that makes particularly planarization difficult, such as wide trench structure (wide trench), in a fine patterning process by a multilayer resist method in a semiconductor-device manufacturing process; and a patterning process and a method for forming a resist underlayer film which use the material.

Solution to Problem

To achieve the object, the present invention provides a resist underlayer film material used in a multilayer resist method, comprising:
(A) at least one compound shown by the following general formula (1); and
(B) an organic solvent,

wherein X independently represents a monovalent organic group shown by the following general formula (2); W represents an organic group with a valency of "n" having 2 to 60 carbon atoms, and containing an "m" number of partial structures each independently shown by the following general formula (3); and "m" and "n" each represent an integer of 1 to 10,

wherein a broken line represents a bonding arm; Z represents an aromatic group with a valency of (k+1) having 6 to 20 carbon atoms; A represents a single bond or —O—$(CH_2)_p$—; "k" represents an integer of 1 to 5; and "p" represents an integer of 1 to 10,

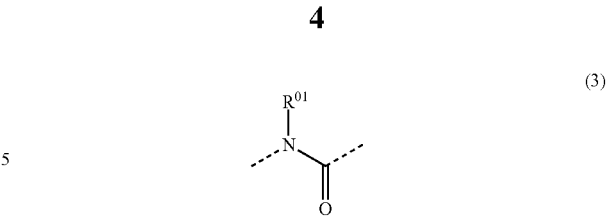

wherein broken lines represent bonding arms, and $R^{01}$ represents a hydrogen atom or a monovalent organic group having 1 to 10 carbon atoms.

Such a resist underlayer film material is capable of forming a resist underlayer film excellent in planarizing property even on a substrate to be processed having a portion that makes particularly planarization difficult, such as wide trench structure (wide trench).

More preferably, A in the general formula (2) is —$OCH_2$—.

Further preferably, the general formula (3) comprises the following general formula (4) or (5),

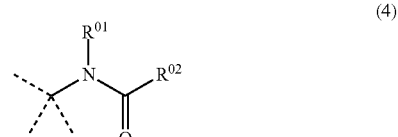

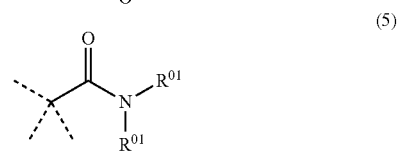

wherein broken lines represent bonding arms; $R^{01}$ represents a hydrogen atom or a monovalent organic group having 1 to 10 carbon atoms; and $R^{02}$ represents a hydrogen atom or a monovalent organic group having 1 to 20 carbon atoms.

Additionally, W in the general formula (1) is preferably represented by any of the following general formulae (6-1) to (6-5),

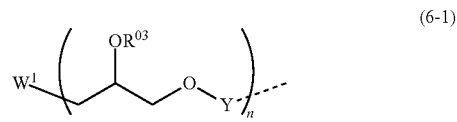

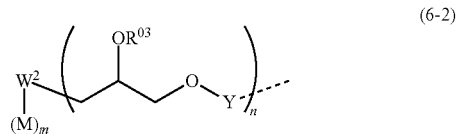

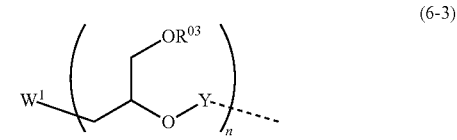

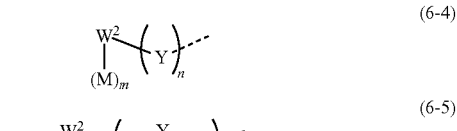

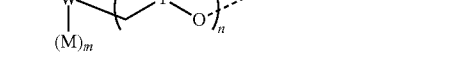

wherein broken lines represent bonding arms; $R^{03}$ represents any of a hydrogen atom, an alkyl group or acyl group having 1 to 20 carbon atoms optionally containing an oxygen atom or nitrogen atom, and the structure of the general formula (3); M represents an organic group containing the structure of the general formula (3); $W^1$ represents an organic group with a valency of "n" having 1 to 57 carbon atoms; $W^2$ represents an organic group with a valency of (m+n); Y represents a single bond or a carbonyl group; and "m" and "n" each represent an integer of 1 to 10.

These resist underlayer film materials can form resist underlayer films having more excellent planarizing property.

Moreover, $W^1$ or $W^2$ in the general formulae (6-1) to (6-5) preferably comprises a structure shown by any of the following formulae.

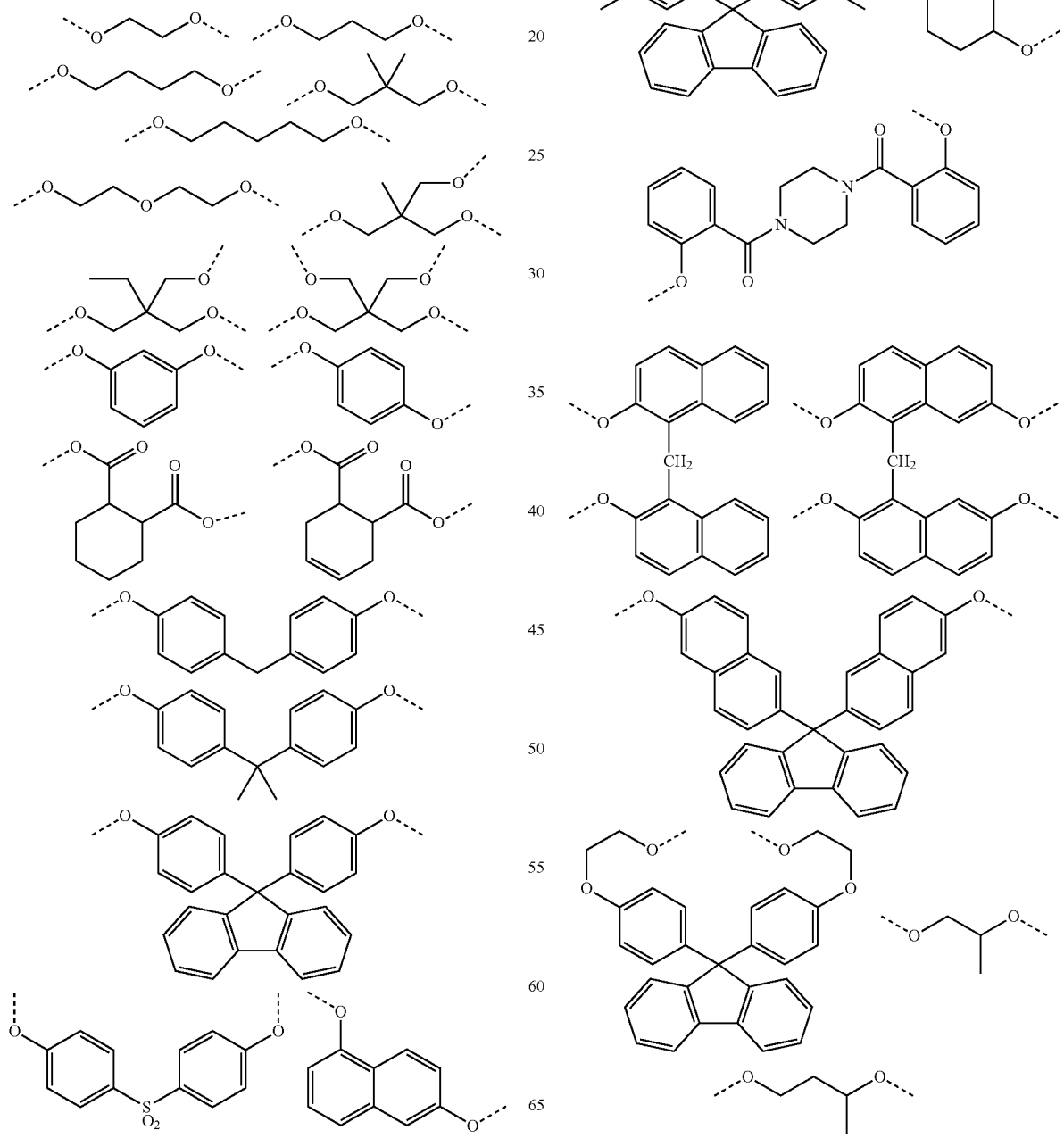

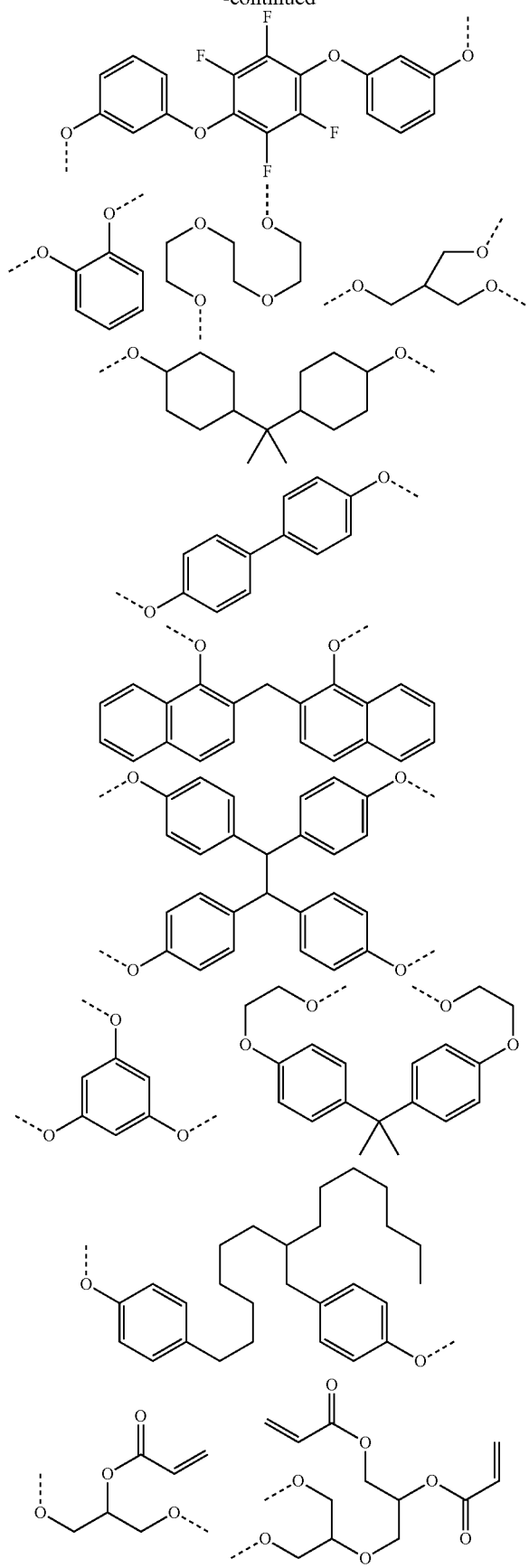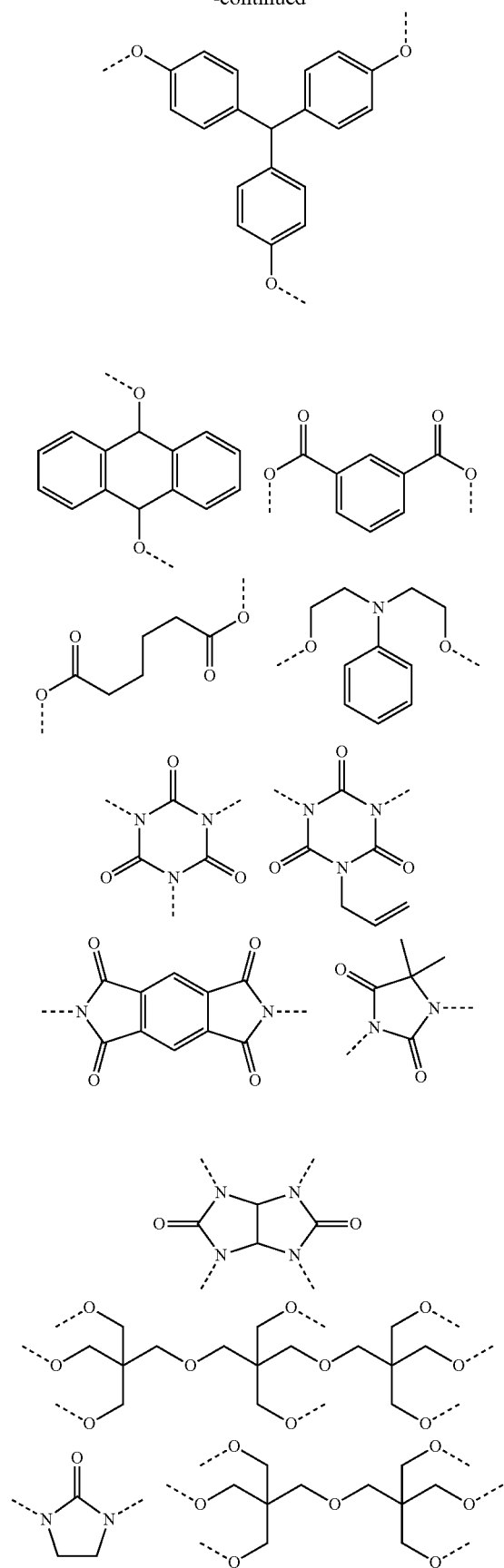

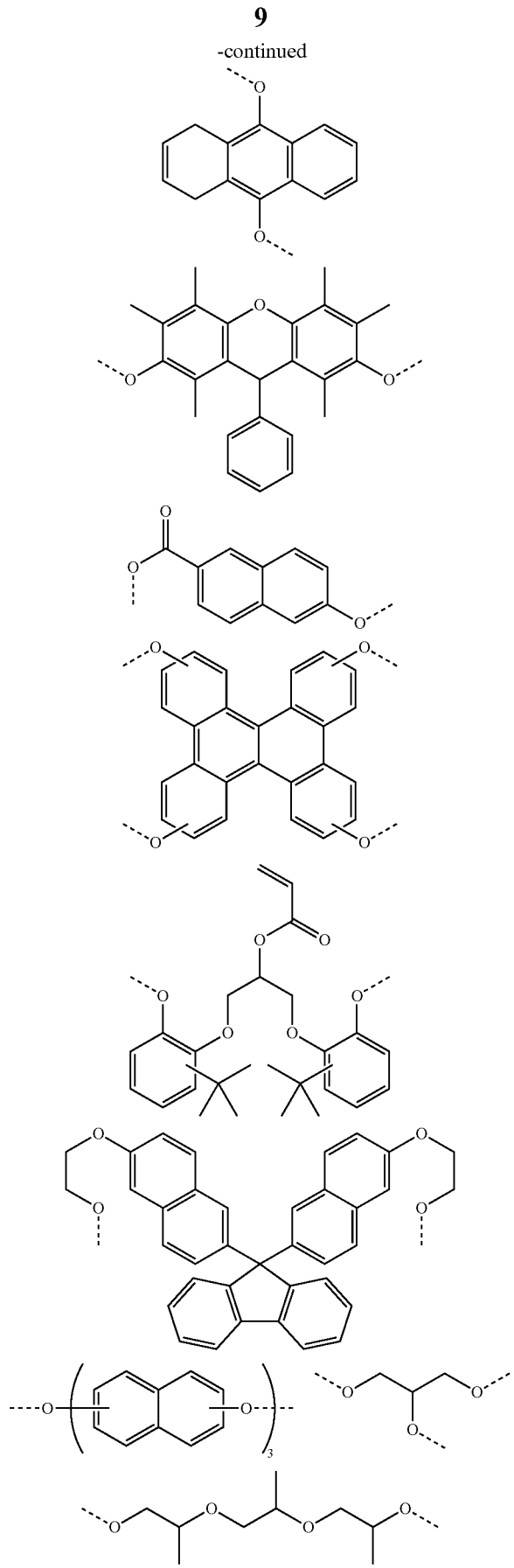

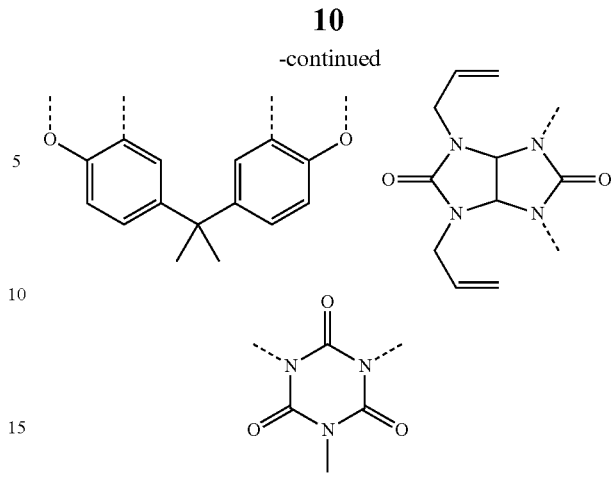

In the formulae, broken lines represent bonding arms.

Such a resist underlayer film material can form a resist underlayer film excellent in planarizing property and can be particularly easily produced.

Further, the organic solvent (B) is preferably a mixture of one or more organic solvents each having a boiling point of lower than 180° C. and one or more organic solvents each having a boiling point of 180° C. or higher.

With such a resist underlayer film material, a resist underlayer film to be formed can have further favorable planarizing property regardless of the design of a substrate to be processed, such as pattern density.

Additionally, the inventive resist underlayer film material may further comprise one or more of (C) an acid generator, (D) a surfactant, (E) a crosslinking agent, (F) a plasticizer, and (G) a pigment.

In this manner, the inventive resist underlayer film material may also contain: (C) an acid generator for promoting curing; (D) a surfactant for enhancing coating property by spin coating; (E) a crosslinking agent for further promoting the crosslinking curing reaction; (F) a plasticizer for further enhancing filling property and planarizing property; and (G) a pigment for adjusting absorption characteristic. These various additives are practically preferable because the presence or absence/selection of these allows fine adjustment of performances, such as film formability, curability, filling property, and optical properties, according to the needs of customers.

Moreover, the inventive resist underlayer film material preferably comprises at least one compound shown by the following general formula (7) as the crosslinking agent (E),

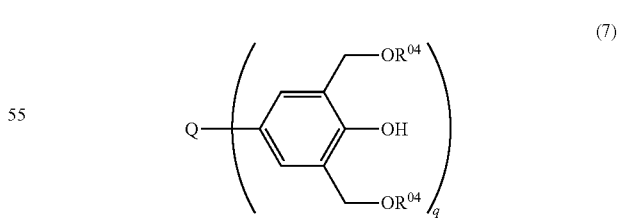

wherein Q represents a single bond, or a hydrocarbon group with a valency of "q" having 1 to 20 carbon atoms;
$R^{04}$ represents a hydrogen atom, or an alkyl group having 1 to 20 carbon atoms; and "q" represents an integer of 1 to 5.

Such a resist underlayer film material has higher crosslinking reactivity. Thus, the solvent resistance of the resist underlayer film is further enhanced. In addition, and the planarizing property and film formability may be enhanced.

Further, the present invention provides a patterning process for forming a pattern in a substrate to be processed, comprising steps of:

(I-1) applying the above-described resist underlayer film material onto a substrate to be processed, followed by heating to form a resist underlayer film;

(I-2) forming a resist upper layer film on the resist underlayer film by using a photoresist material;

(I-3) subjecting the resist upper layer film to pattern exposure and then development with a developer to form a pattern in the resist upper layer film;

(I-4) transferring the pattern to the resist underlayer film by dry etching while using the resist upper layer film having the formed pattern as a mask; and (I-5) processing the substrate to be processed while using the resist underlayer film having the formed pattern as a mask to form the pattern in the substrate to be processed.

Furthermore, the present invention provides a patterning process for forming a pattern in a substrate to be processed, comprising steps of:

(II-1) applying the above-described resist underlayer film material onto a substrate to be processed, followed by heating to form a resist underlayer film;

(II-2) forming a resist middle layer film on the resist underlayer film;

(II-3) forming a resist upper layer film on the resist middle layer film by using a photoresist material;

(II-4) subjecting the resist upper layer film to pattern exposure and then development with a developer to form a pattern in the resist upper layer film;

(II-5) transferring the pattern to the resist middle layer film by dry etching while using the resist upper layer film having the formed pattern as a mask;

(II-6) transferring the pattern to the resist underlayer film by dry etching while using the resist middle layer film having the transferred pattern as a mask; and (II-7) processing the substrate to be processed while using the resist underlayer film having the formed pattern as a mask to form the pattern in the substrate to be processed.

Furthermore, the present invention provides a patterning process for forming a pattern in a substrate to be processed, comprising steps of:

(III-1) applying the above-described resist underlayer film material onto a substrate to be processed, followed by heating to form a resist underlayer film;

(III-2) forming an inorganic hard mask middle layer film selected from a silicon oxide film, a silicon nitride film, and a silicon oxynitride film on the resist underlayer film;

(III-3) forming an organic thin film on the inorganic hard mask middle layer film;

(III-4) forming a resist upper layer film on the organic thin film by using a photoresist material;

(III-5) subjecting the resist upper layer film to pattern exposure and then development with a developer to form a pattern in the resist upper layer film;

(III-6) transferring the pattern to the organic thin film and the inorganic hard mask middle layer film by dry etching while using the resist upper layer film having the formed pattern as a mask;

(III-7) transferring the pattern to the resist underlayer film by dry etching while using the inorganic hard mask middle layer film having the transferred pattern as a mask; and (III-8) processing the substrate to be processed while using the resist underlayer film having the formed pattern as a mask to form the pattern in the substrate to be processed.

As described, the inventive resist underlayer film material can be suitably employed in various patterning processes, such as 2-layer resist process, 3-layer resist process using a resist middle layer film, and 4-layer resist process additionally using an organic thin film. These patterning processes enable effective reductions in unevenness and steps of a substrate to be processed by forming a resist underlayer film, and thus are suitable for photolithography of a resist upper layer film.

Moreover, in the inventive patterning processes, the substrate to be processed may have a structure or step with a height of 30 nm or more.

Because of the use of the inventive resist underlayer film material capable of forming a resist underlayer film having high filling and planarizing properties, the inventive patterning processes are particularly useful for fine processing of a substrate having such a structure or step.

Additionally, the present invention provides a method for forming a resist underlayer film that serves as an organic planarizing film employed in a semiconductor device manufacturing process, the method comprising:

spin-coating a substrate to be processed with the above-described resist underlayer film material; and heating the substrate coated with the resist underlayer film material at a temperature of 100° C. or higher and 600° C. or lower for 10 to 600 seconds to form a cured film.

Further, the present invention provides a method for forming a resist underlayer film that serves as an organic planarizing film employed in a semiconductor device manufacturing process, the method comprising:

spin-coating a substrate to be processed with the above-described resist underlayer film material; and heating the substrate coated with the resist underlayer film material under an atmosphere with an oxygen concentration of 1% or more and 21% or less to form a cured film.

Such methods make it possible to more considerably suppress mixing with an upper layer film by promoting the crosslinking reaction that takes place when the resist underlayer film is formed. Moreover, by appropriately adjusting the heating temperature, time, and oxygen concentration within the above-described ranges, it is possible to obtain a resist underlayer film having suitable filling, planarizing, and curing properties in accordance with use.

Furthermore, the present invention provides a method for forming a resist underlayer film that serves as an organic planarizing film employed in a semiconductor device manufacturing process, the method comprising:

spin-coating a substrate to be processed with the above-described resist underlayer film material; and heating the substrate coated with the resist underlayer film material under an atmosphere with an oxygen concentration of less than 1% to form a cured film.

According to such a method, even when a substrate to be processed contains a material that is unstable under heating condition in an oxygen atmosphere, the substrate to be processed is not degraded, and the method is useful and makes it possible to more considerably suppress mixing with an upper layer film by promoting the crosslinking reaction when the resist underlayer film is formed.

In this event, the substrate to be processed may have a structure or step with a height of 30 nm or more.

Because of the use of the inventive resist underlayer film material capable of forming a resist underlayer film having high filling and planarizing properties, the inventive methods for forming a resist underlayer film are particularly suitable for forming a resist underlayer film on a substrate having such a structure or step.

Advantageous Effects of Invention

As described above, the resist underlayer film material, the patterning processes, and the methods for forming a resist underlayer film according to the present invention are particularly suitably utilized in multilayer resist processes including planarizing a stepped and uneven substrate to be processed, and are quite useful in fine patterning for manufacturing a semiconductor device. The present invention makes it possible to provide: a resist underlayer film material having appropriate etching and optical properties and being capable of forming a resist underlayer film excellent in planarizing property even when a substrate to be processed has a portion that makes particularly planarization difficult, such as wide trench structure (wide trench), especially in a fine patterning process by a multilayer resist method in a semiconductor-device manufacturing process; and patterning processes and methods for forming a resist underlayer film which use the material.

BRIEF DESCRIPTION OF DRAWINGS

FIG. 1 is an explanatory diagram illustrating an example of an inventive patterning process according to a 3-layer resist process.

FIG. 2 is an explanatory diagram illustrating a method for evaluating filling property in Examples.

FIG. 3 is an explanatory diagram illustrating a method for evaluating planarizing property in Examples.

DESCRIPTION OF EMBODIMENTS

As noted above, there have been demands for: a resist underlayer film material having excellent filling property and appropriate etching and optical properties, and being capable of forming a resist underlayer film excellent in planarizing property even on a substrate to be processed having a portion, such as wide trench structure (wide trench), that makes particularly planarization difficult in a fine patterning process by a multilayer resist method in a semiconductor-device manufacturing process; and a patterning process and a method for forming a resist underlayer film which use the material.

The present inventors have searched various resist underlayer film materials and patterning processes in order to achieve high filling/planarization through underlayer film formation in multilayer lithography using a resist underlayer film. Consequently, the inventors have found that a resist underlayer film material mainly containing a compound with a certain structure, a patterning process and a method for forming a resist underlayer film which use the material are very effective. These findings have led to the completion of the present invention.

Specifically, the inventive resist underlayer film material is a resist underlayer film material used in a multilayer resist method, comprising:

(A) at least one compound shown by the following general formula (1); and (B) an organic solvent,

wherein X independently represents a monovalent organic group shown by the following general formula (2); W represents an organic group with a valency of "n" having 2 to 60 carbon atoms, and containing an "m" number of partial structures each independently shown by the following general formula (3); and "m" and "n" each represent an integer of 1 to 10,

wherein a broken line represents a bonding arm; Z represents an aromatic group with a valency of (k+1) having 6 to 20 carbon atoms; A represents a single bond or —O—$(CH_2)_p$—; "k" represents an integer of 1 to 5; and "p" represents an integer of 1 to 10,

wherein broken lines represent bonding arms, and $R^{01}$ represents a hydrogen atom or a monovalent organic group having 1 to 10 carbon atoms.

Hereinafter, the present invention will be described in detail, but the present invention is not limited thereto.

<Resist Underlayer Film Material>

The inventive resist underlayer film material is a resist underlayer film material to be used in a multilayer resist method as described above, and contains:

(A) at least one compound shown by the following general formula (1); and (B) an organic solvent.

In the formula, X independently represents a monovalent organic group shown by the following general formula (2). W represents an organic group with a valency of "n" having 2 to 60 carbon atoms, and containing an "m" number of partial structures each independently shown by the following general formula (3). "m" and "n" each represent an integer of 1 to 10.

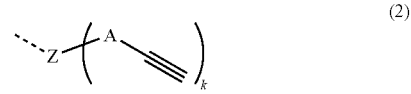

In the formula, a broken line represents a bonding arm. Z represents an aromatic group with a valency of (k+1) having 6 to 20 carbon atoms. "A" represents a single bond or —O—(CH$_2$)$_p$—. "k" represents an integer of 1 to 5. "p" represents an integer of 1 to 10,

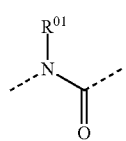

(3)

In the formula, broken lines represent bonding arms. R$^{01}$ represents a hydrogen atom or a monovalent organic group having 1 to 10 carbon atoms.

The inventive resist underlayer film material containing the compound shown by the general formula (1) is excellent in flowability and substrate affinity. Hence, the inventive resist underlayer film material is presumably capable of forming a resist underlayer film excellent in planarizing property even on a substrate to be processed having a portion, such as wide trench structure (wide trench), that makes particularly planarization difficult.

In the general formula (1), each X is independently a monovalent organic group shown by the general formula (2). In the general formula (2), a broken line represents a bonding arm. Z represents an aromatic group having a valency of (k+1) and 6 to 20 carbon atoms. Z is a group having a valency of (k+1) and a structure which corresponds to an aromatic compound having 6 to 20 carbon atoms but (k+1) hydrogen atoms having been removed from the aromatic compound. The aromatic compound having 6 to 20 carbon atoms is preferably benzene, naphthalene, phenanthrene, anthracene, pyrene, biphenyl, toluene, xylene, methylnaphthalene, or fluorene, particularly preferably benzene or fluorene. "k" is an integer of 1 to 5. To obtain more favorable planarizing property, "k" is more preferably 1 to 3. "A" is a single bond or —O—(CH$_2$)$_p$—. "p" is an integer of 1 to 10. "A" is more preferably —OCH$_2$— to obtain favorable planarizing property.

In the inventive resist underlayer film material, X in the general formula (1) is a monovalent organic group shown by the general formula (2). Hence, when the underlayer film is cured, the film shrinks less, and degradation of planarizing property due to the shrinkage is suppressed. This presumably enables high planarizing property.

In the general formula (1), W is an organic group with a valency of "n" having 2 to 60 carbon atoms, and contains "m" partial structures each independently shown by the general formula (3). "m" and "n" are each an integer of 1 to 10. In other words, W is an organic group having a valency of 1 to 10 and a structure which corresponds to an organic compound having 2 to 60 carbon atoms but 1 to 10 hydrogen atom(s) having been removed from the organic compound. The organic compound having 2 to 60 carbon atoms and a structure which corresponds to W with additional 1 to 10 hydrogen atom(s) contains the "m" number of partial structures each independently shown by the general formula (3), and may contain a linear, branched or cyclic, saturated or unsaturated hydrocarbon group, an aromatic group, a heteroaromatic group, an ether group, a hydroxyl group, an ester group, a ketone group, an amino group, a halogen group, a sulfide group, a carboxyl group, a sulfo group, an imide group, a cyano group, an aldehyde group, an imino group, a urea group, a carbamate group, a carbonate group, a nitro group, or a sulfone group. To achieve both favorable planarizing property and sufficient thermosetting property, "n" is more preferably 2 to 4. In the general formula (3), broken lines represent bonding arms. R$^{01}$ is a hydrogen atom or a monovalent organic group having 1 to 10 carbon atoms. R$^{01}$ is more preferably a hydrogen atom or a methyl group.

Since W in the general formula has the partial structure shown by the general formula (3), the affinity between the inventive resist underlayer film material and a substrate to be processed is presumably increased, so that favorable planarizing property is exhibited.

Properties such as etching resistance, heat resistance, optical properties, polarity, and flexibility of the resist underlayer film material can be adjusted by appropriately selecting W, X, and "n" in the compound of the general formula (1) according to the usage. Regarding the optical properties among these, when the resist underlayer film material has appropriate optical properties at 193 nm wavelength, reflection light can be suppressed during exposure in multilayer ArF lithography, and excellent resolution can be achieved. Note that, to suppress reflection light, the resist underlayer film material has, as the optical constant, a refractive index n of preferably about 1.4 to 1.9, and an extinction coefficient k preferably in a range of 0.1 to 0.5.

In the present invention, one kind of the compound of the general formula (1) may be used singly, or two or more kinds thereof may be mixed and used. Alternatively, a mixture containing the compound shown by the general formula (1) may be used. When such a mixture is used, the proportion of the compound shown by the general formula (1) in the whole solid content excluding the solvent of the resist underlayer film material is preferably 10 mass % or more. The proportion is more preferably 20 mass % or more. When the proportion is 10 mass % or more, sufficient blending effect is obtained. The compound of the general formula (1) has a formula weight of preferably 300 to 5,000, particularly preferably 500 to 2,500. With the molecular weight of 300 or more, excellent film formability is obtained, and the apparatus will not be contaminated by increase in sublimation products during curing. When the molecular weight is 5,000 or less, excellent planarizing and filling properties is obtained. Note that, in the present invention, the molecular weight can be obtained as a weight-average molecular weight (Mw) in terms of polystyrene by gel permeation chromatography (GPC) using tetrahydrofuran as an eluent.

In the present invention, the partial structure shown by the general formula (3) is more preferably a structure shown by the following general formula (4) or (5).

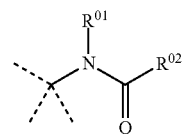

(4)

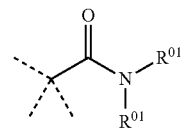

(5)

In the formulae, broken lines represent bonding arms. R$^{01}$ represents a hydrogen atom or a monovalent organic group having 1 to 10 carbon atoms. $R^{02}$ represents a hydrogen atom or a monovalent organic group having 1 to 20 carbon atoms.

In the general formulae (4) and (5), each broken line represents a bonding arm. $R^{01}$ is as defined above. $R^{02}$ is a hydrogen atom or a monovalent organic group having 1 to 20 carbon atoms. $R^{02}$ is more preferably a hydrogen atom or a methyl group.

When W in the general formula has a partial structure shown by the general formula (4) or (5), the affinity between the inventive resist underlayer film material and a substrate to be processed is presumably further increased, so that more favorable planarizing property is exhibited.

In the present invention, W in the general formula (1) preferably has a structure shown by any of the following general formulae (6-1) to (6-5).

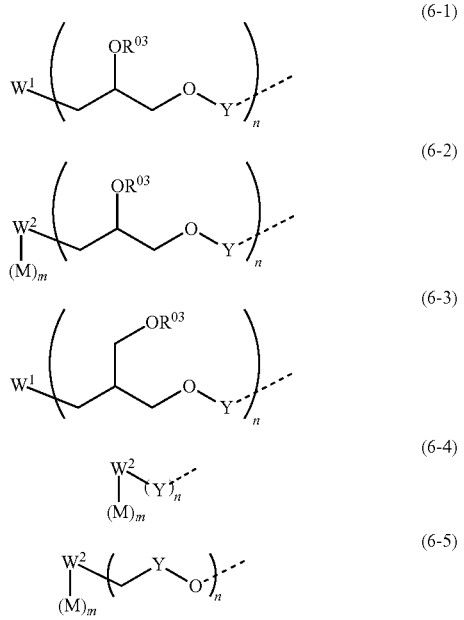

In the formulae, broken lines represent bonding arms. $R^{03}$ represents any of a hydrogen atom, an alkyl group or acyl group having 1 to 20 carbon atoms optionally containing an oxygen atom or nitrogen atom, and the structure of the general formula (3). M represents an organic group containing the structure of the general formula (3). $W^1$ represents an organic group with a valency of "n" having 1 to 57 carbon atoms. $W^2$ represents an organic group with a valency of (m+n). Y represents a single bond or a carbonyl group. "m" and "n" each represent an integer of 1 to 10.

In the general formulae (6-1) to (6-5), $R^{03}$ may be a hydrogen atom, or an alkyl group or acyl group having 1 to 20 carbon atoms optionally containing an oxygen atom or nitrogen atom and/or the structure of the general formula (3). More specific examples of $R^{03}$ can include, but are not limited to, a hydrogen atom, a methyl group, a methoxymethyl group, a 1-ethoxyethyl group, a 1-(2-ethylhexyloxy) ethyl group, a 2-tetrahydropyranyl group, an allyl group, a benzyl group, a propargyl group, a formyl group, an acetyl group, a propionyl group, a butyryl group, a hexanoyl group, an icosanoyl group, an acryloyl group, a methacryloyl group, a propioloyl group, a methoxyacetyl group, a benzoyl group, a 4-acetamidobenzoyl group, a carbamoyl group, an N-methylcarbamoyl group, and an N,N-dimethylcarbamoyl group.

In the case where W is shown by the general formula (6-1) or (6-3), $R^{03}$ is preferably an acyl group containing the structure of the general formula (3). In the case where W is shown by the general formula (6-2), $R^{03}$ is preferably a hydrogen atom, an acryloyl group, or an acetyl group, and is more preferably a hydrogen atom.

$W^1$ is an organic group with a valency of "n" having 1 to 57 carbon atoms. In other words, $W^1$ is an organic group having a valency of 1 to 10 and a structure which corresponds to an organic compound having 1 to 57 carbon atoms but 1 to 10 hydrogen atom(s) having been removed from the organic compound. In this case, the organic compound having 1 to 57 carbon atoms and a structure which corresponds to $W^1$ with additional 1 to 10 hydrogen atom(s) may contain a linear, branched or cyclic, saturated or unsaturated hydrocarbon group, an aromatic group, a heteroaromatic group, an ether group, a hydroxyl group, an ester group, a ketone group, an amino group, a halogen group, a sulfide group, a carboxyl group, a sulfo group, an imide group, a cyano group, an aldehyde group, an imino group, a urea group, a carbamate group, a carbonate group, a nitro group, or a sulfone group. $W^2$ is an organic group having a valency of (m+n).

To achieve both favorable planarizing property and sufficient thermosetting property, "n" is more preferably 2 to 4. Y is a single bond or a carbonyl group. Y is more preferably a carbonyl group. M is an organic group having an amide group of the general formula (3).

A preferable example of M in the general formulae (6-2), (6-4), and (6-5) is shown by the following general formula.

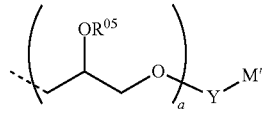

In the formula, a broken line represents a bonding arm. M' represents an organic group having 1 to 20 carbon atoms containing the structure of the general formula (4) or (5). $R^{05}$ is the same as $R^{03}$. Y is as defined above. "a" represents 0 or 1.

M' is an organic group having 1 to 20 carbon atoms and containing the structure of the general formula (4) or (5). Examples of $R^{05}$ include those exemplified as $R^{03}$. Preferably, $R^{05}$ is a hydrogen atom, an acryloyl group, or an acetyl group.

Properties such as etching resistance, heat resistance, optical constant, polarity, flexibility, and curability can be adjusted by appropriately selecting $R^{03}$, $W^1$, $W^2$, Y, M, "m", and "n" according to the usage.

In the present invention, $W^1$ or $W^2$ in the general formulae (6-1) to (6-5) more preferably has a structure shown by any of the following formulae.

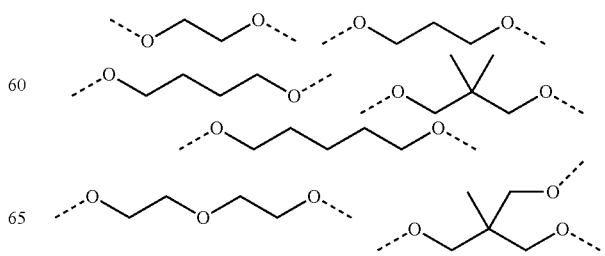

-continued
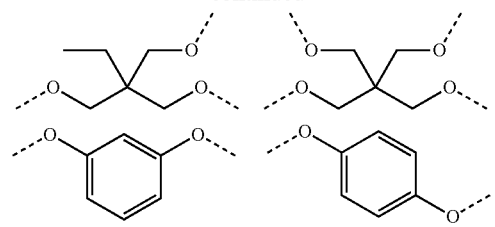
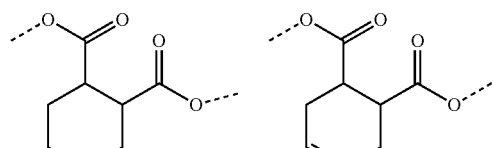
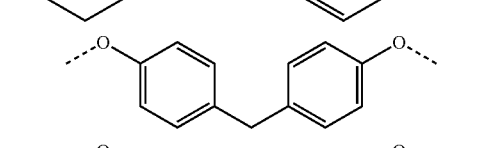
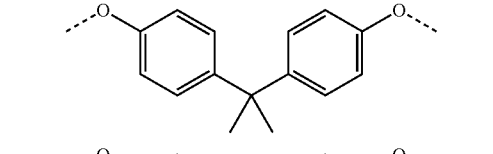
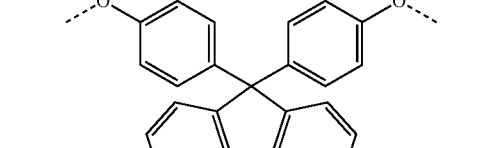
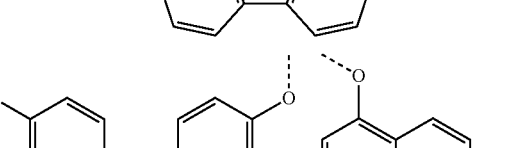
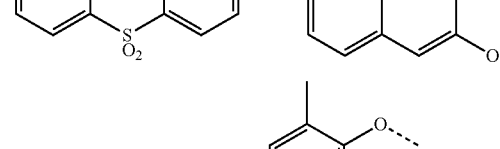
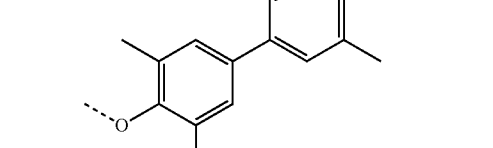
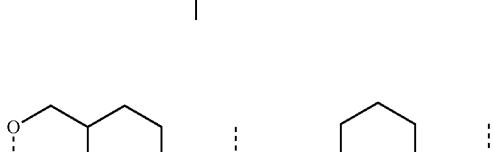
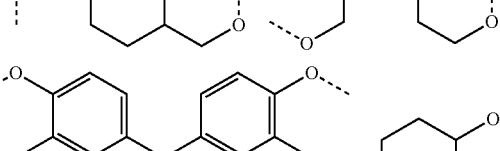
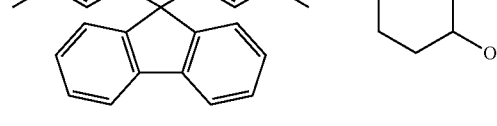
-continued
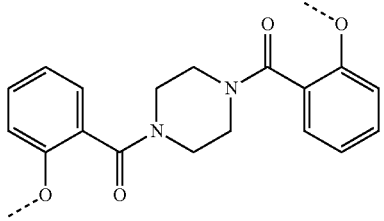
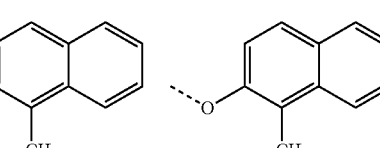
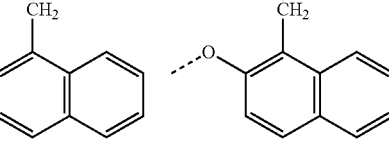
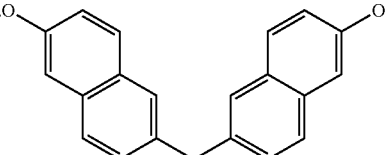
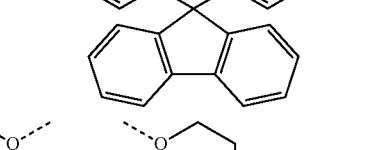
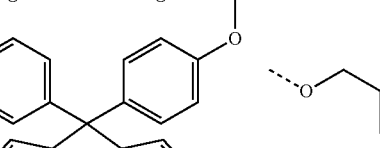
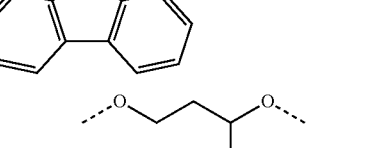
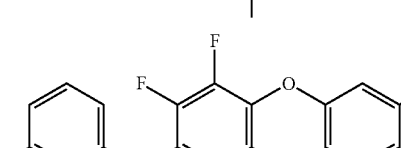
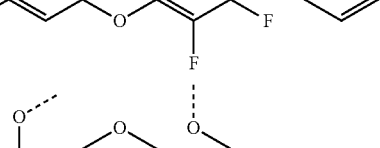
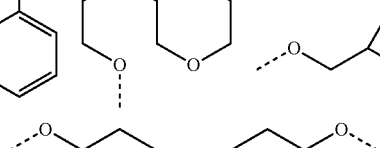
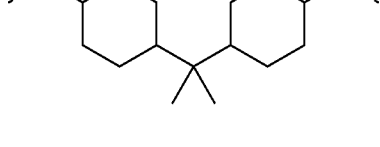

-continued
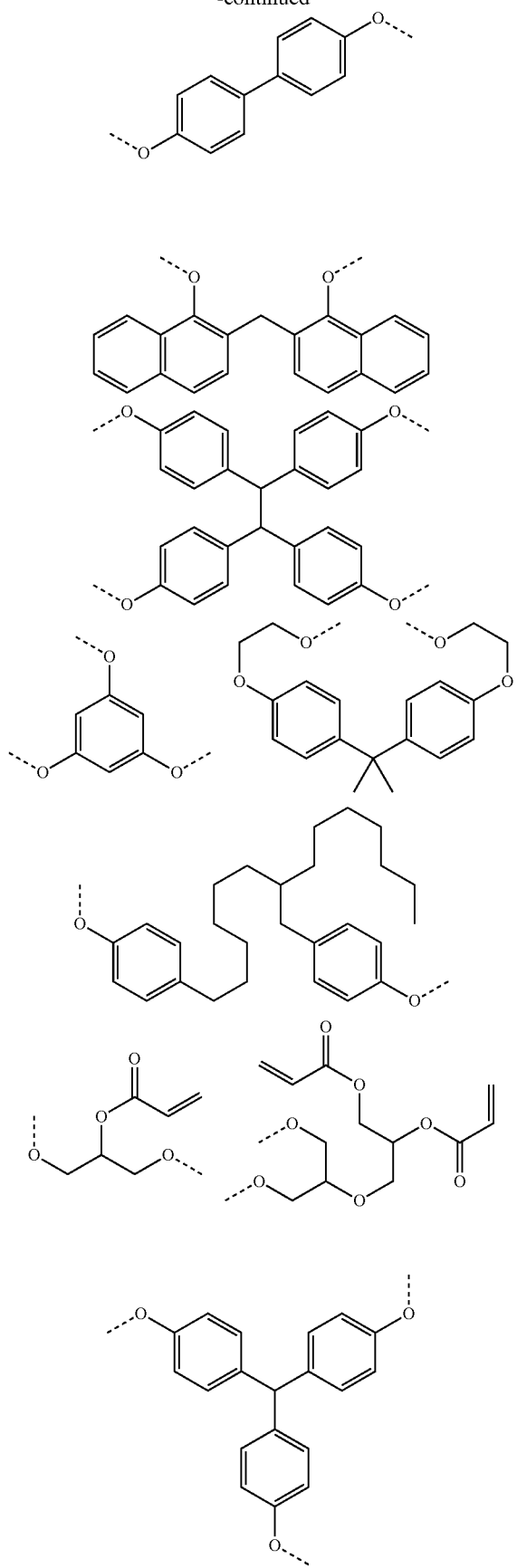
-continued
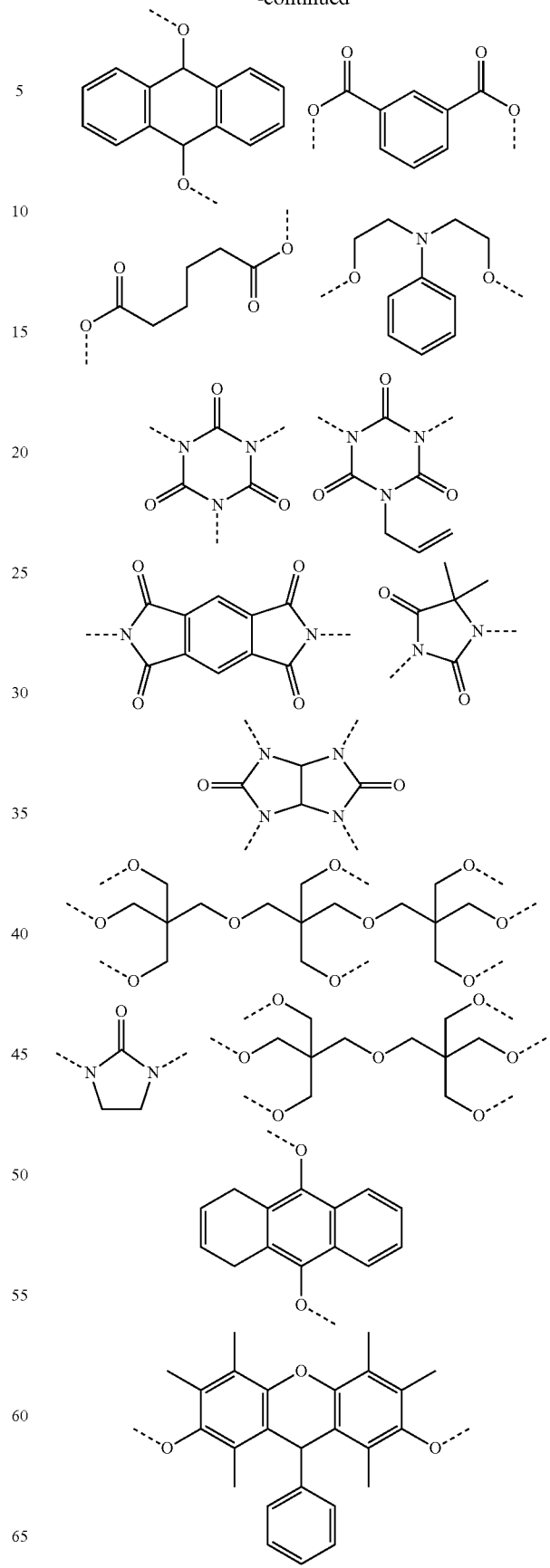

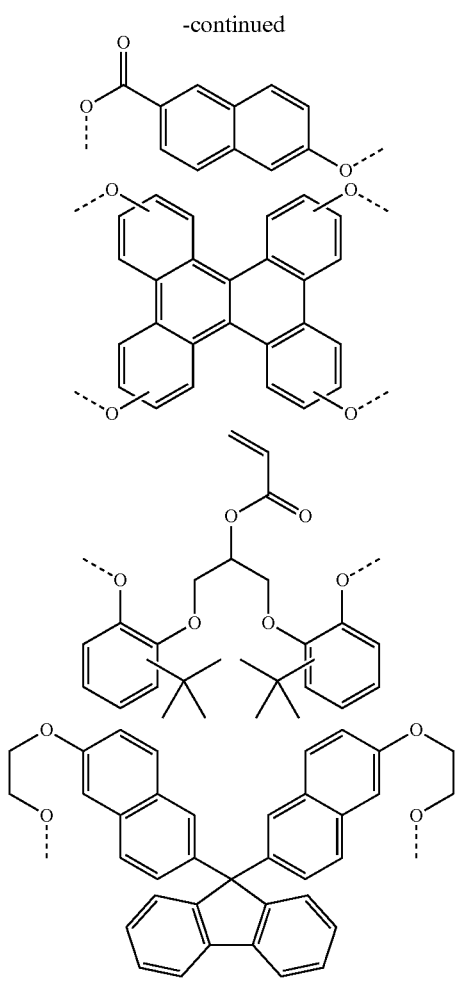
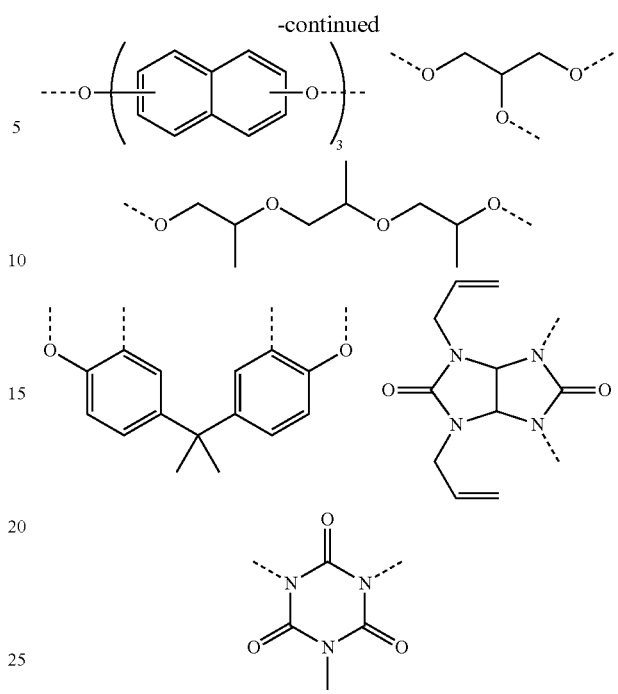

In these formulae, broken lines represent bonding arms.

Such resist underlayer film materials can form resist underlayer films having excellent planarizing property and can be manufactured particularly easily.

Specific examples of the compound shown by the general formula (1) include the following compounds, but are not limited thereto. In the following formulae, Ac represents an acetyl group, and Me represents a methyl group. The same applies hereinafter.

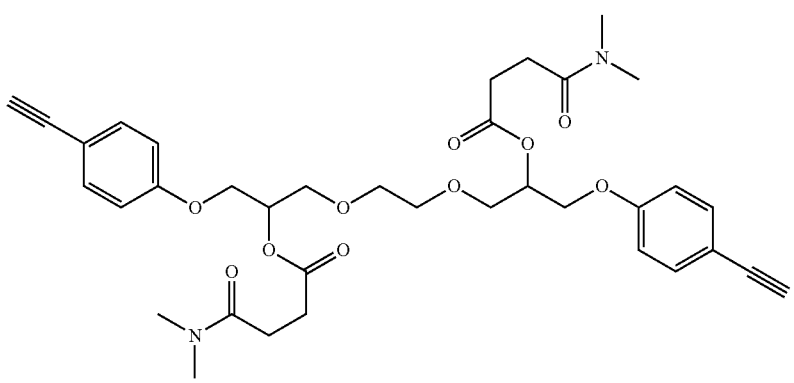
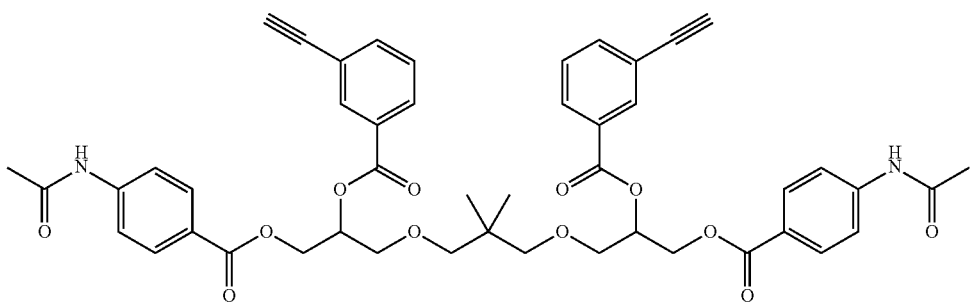

25 26
-continued
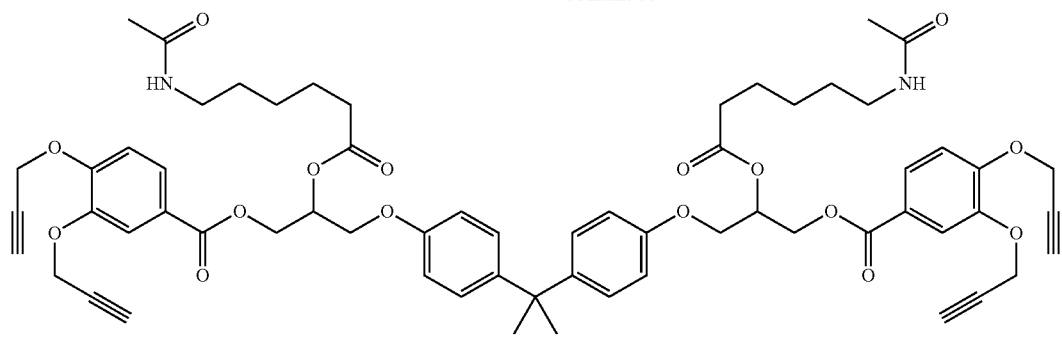
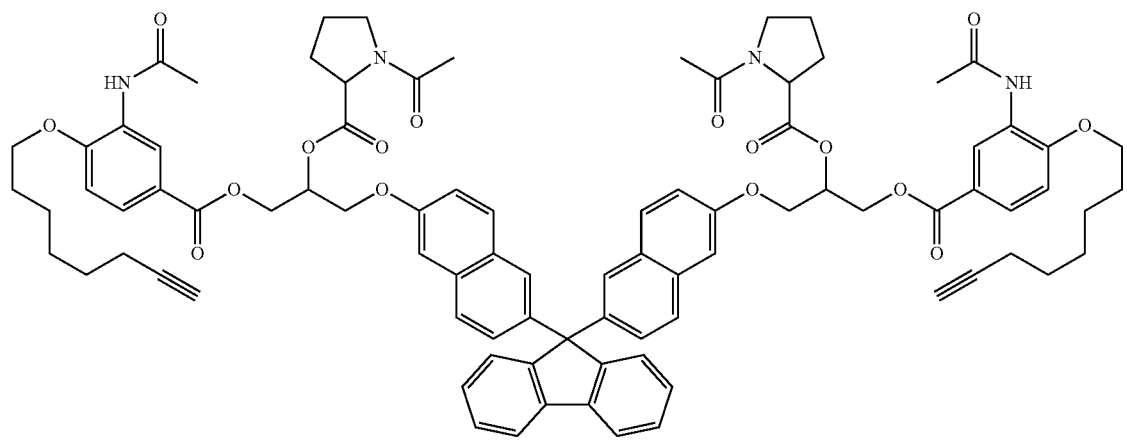
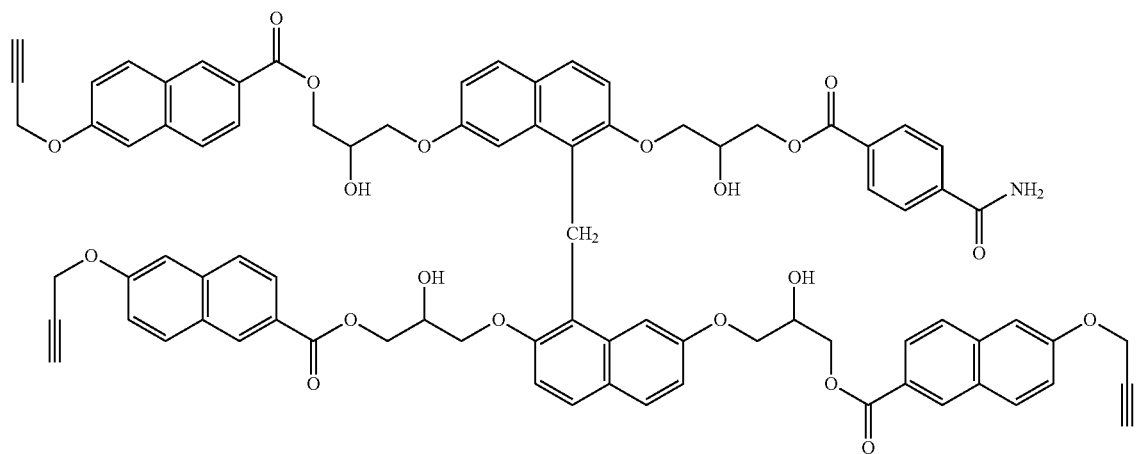
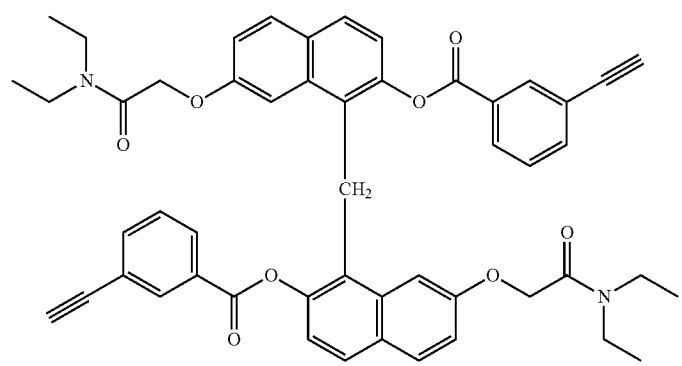

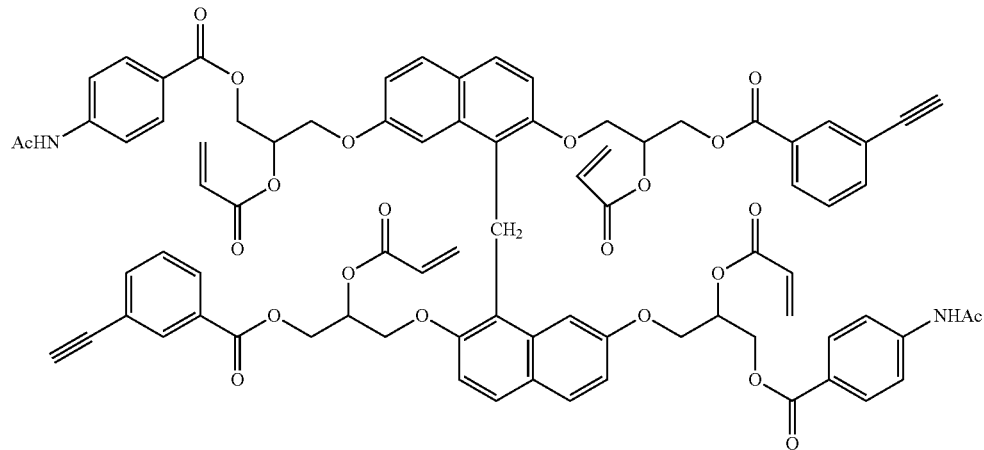
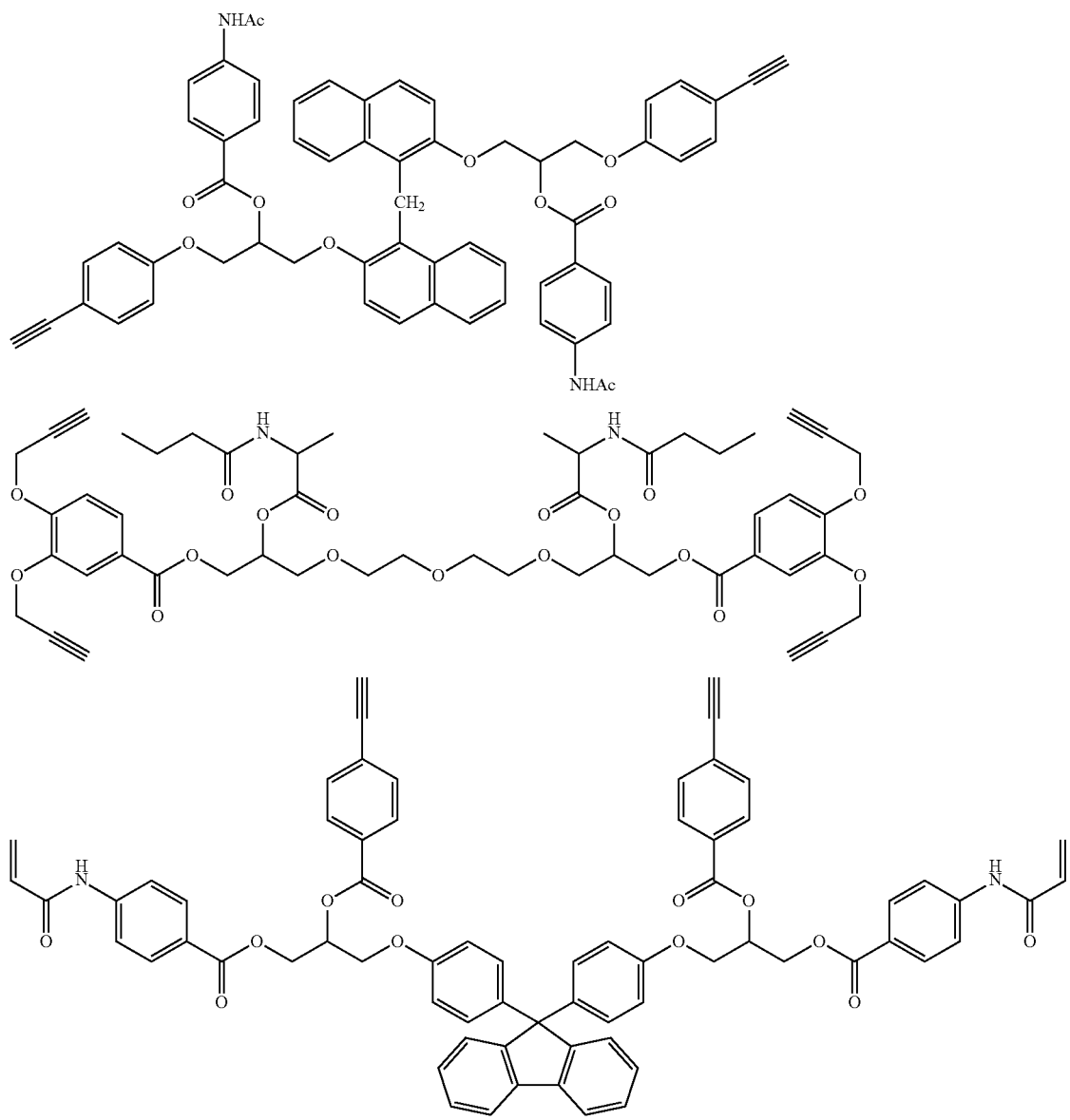

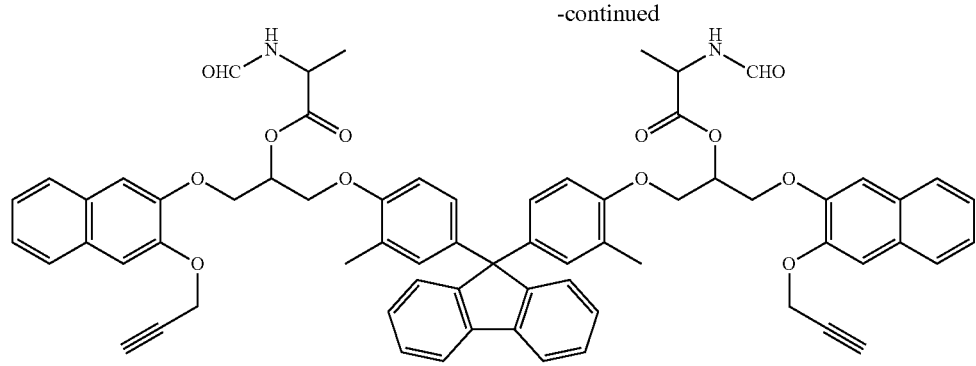
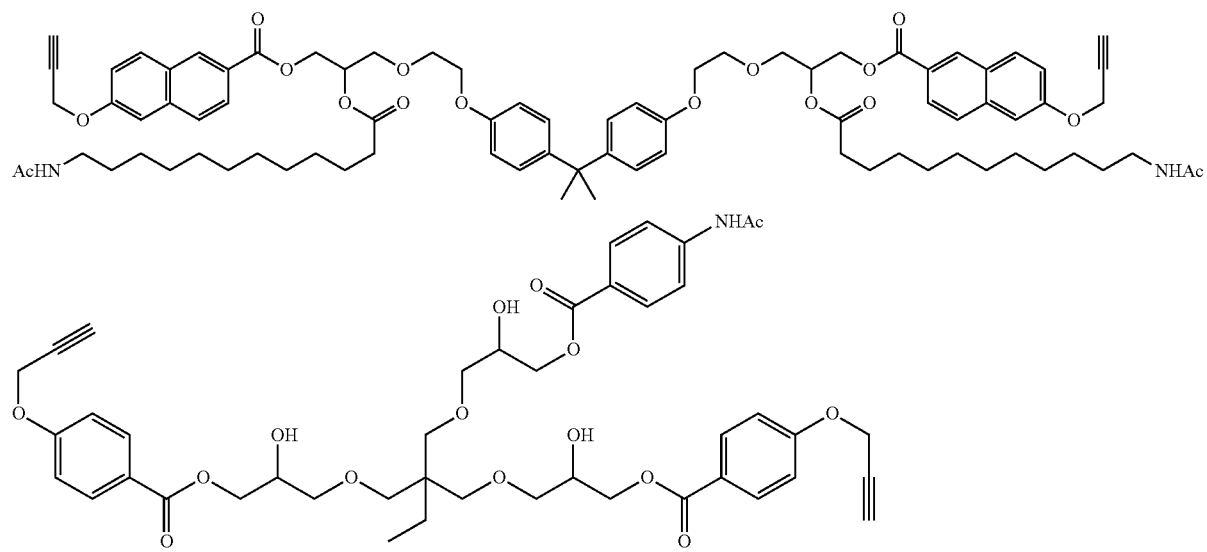
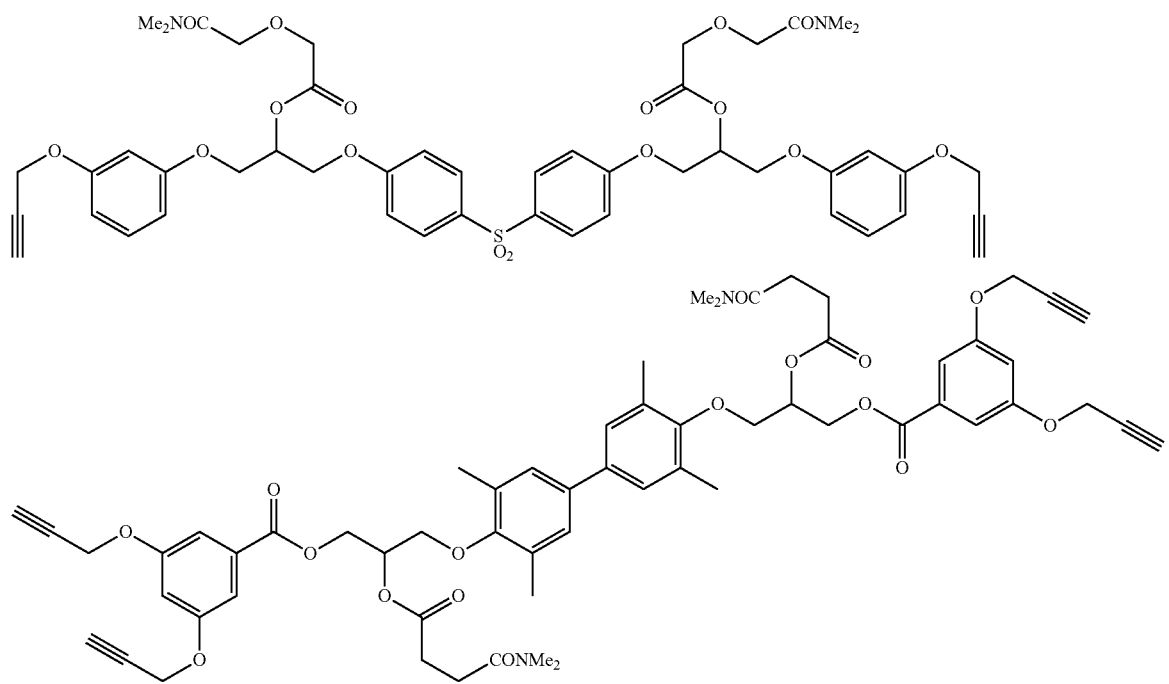

31    32
-continued
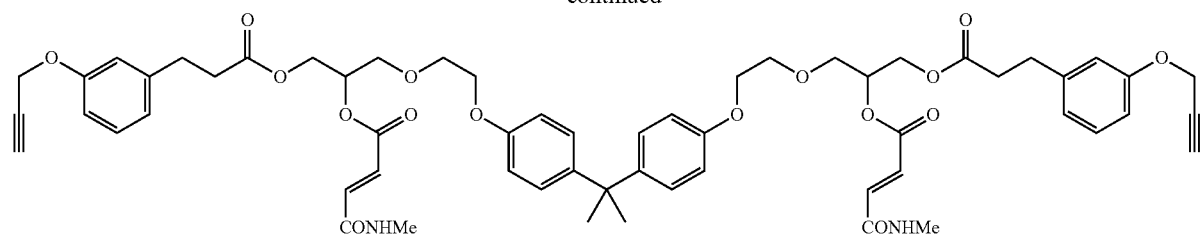
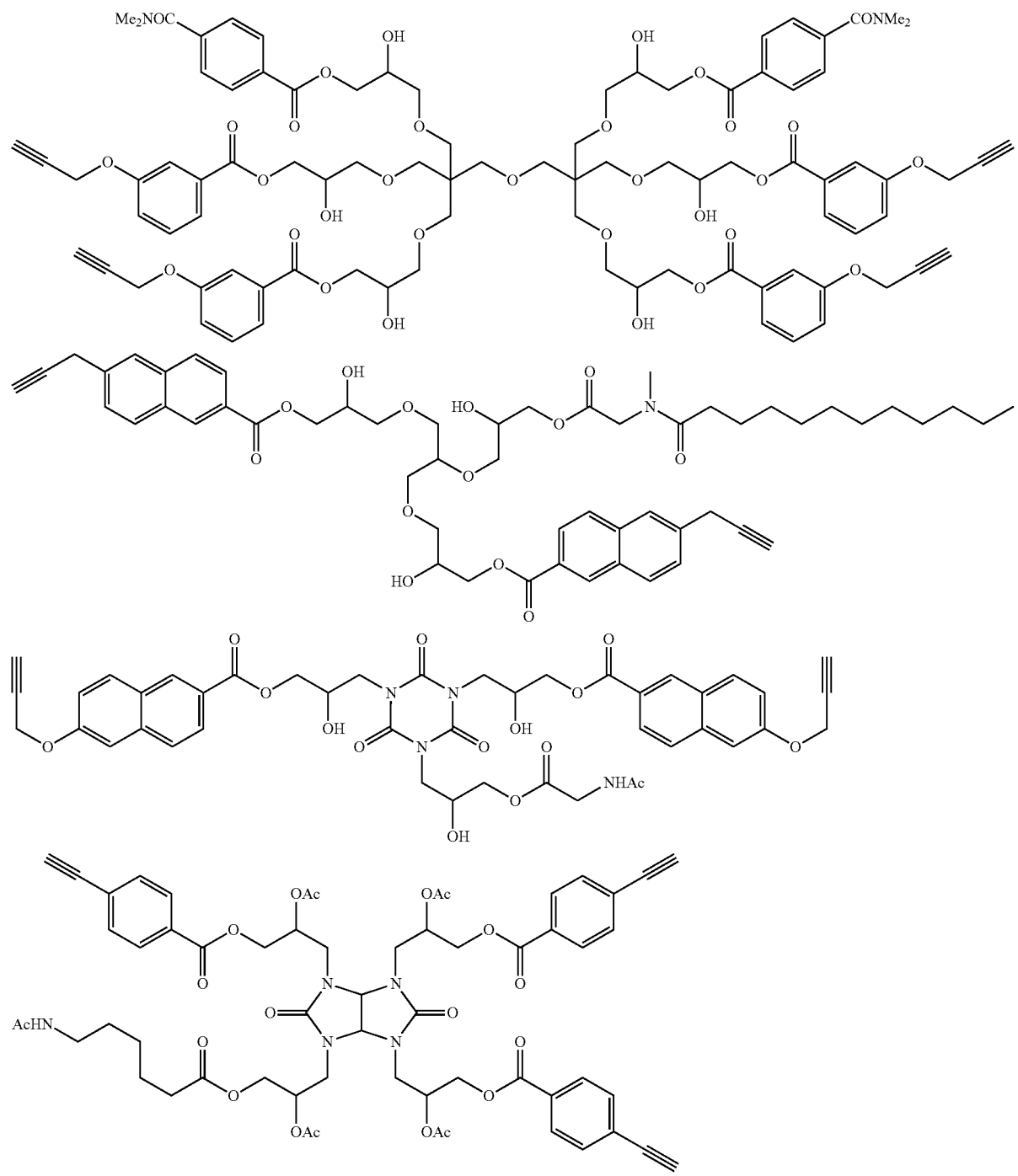

The inventive resist underlayer film material can be further blended with another substance in addition to the compound shown by the general formula (1). The blend substance is mixed with the compound shown by the general formula (1), and serves to enhance film formability by spin coating and filling property for a substrate having a step(s). The substance that may be mixed in this case is not particularly limited, and known substances can be used. Specifically, the substance is preferably an acrylic resin, a styrene resin, a phenol resin, a polyether resin, an epoxy resin, or a compound having a phenolic hydroxyl group. The blend substance is blended in an amount of preferably 1 to 100 parts by mass, more preferably 2 to 50 parts by mass, based on 100 parts by mass of the compound shown by the general formula (1).

The organic solvent (B) usable in the inventive resist underlayer film material is not particularly limited, as long as it is capable of dissolving one or two or more kinds of the compound (A) shown by the general formula (1). Preferably, the organic solvent (B) is capable of dissolving (C) an acid generator, (D) a surfactant, (E) a crosslinking agent, (F) a plasticizer, and (G) a pigment, which are described later.

Specifically, solvents disclosed in paragraphs [0091] to [0092] of JP 2007-199653 A can be added. More specifically, it is preferable to use propylene glycol monomethyl ether acetate, propylene glycol monomethyl ether, propylene glycol monoethyl ether, propylene glycol monopropyl ether, 2-heptanone, cyclopentanone, cyclohexanone, and γ-butyrolactone, or a mixture containing one or more of these.

It is desirable to adjust the amount of the organic solvent blended, depending on an intended thickness of the resist underlayer film. Generally, the amount is in a range of 100 to 50,000 parts by mass based on 100 parts by mass of the compound of the general formula (1).

Moreover, in the inventive resist underlayer film material, the organic solvent (B) is preferably a mixture of one or more organic solvents each having a boiling point of lower than 180° C. and one or more organic solvents each having a boiling point of 180° C. or higher (hereinafter also referred to as "high-boiling-point solvent(s)").

Specific examples of the organic solvents having a boiling point of lower than 180° C. can include propylene glycol monomethyl ether acetate, propylene glycol monomethyl ether, propylene glycol monoethyl ether, propylene glycol monopropyl ether, 2-heptanone, cyclopentanone, and cyclohexanone.

The organic solvents having a boiling point of 180° C. or higher are not particularly limited to hydrocarbons, alcohols, ketones, esters, ethers, chlorinated solvents, and so forth, as long as the high-boiling-point solvents are capable of dissolving each component of the inventive resist underlayer film material. Specific examples thereof can include 1-octanol, 2-ethylhexanol, 1-nonanol, 1-decanol, 1-undecanol, ethylene glycol, 1,2-propylene glycol, 1,3-butylene glycol, 2,4-pentanediol, 2-methyl-2,4-pentanediol, 2,5-hexanediol, 2,4-heptanediol, 2-ethyl-1,3-hexanediol, diethylene glycol, dipropylene glycol, triethylene glycol, tripropylene glycol, glycerin, n-nonyl acetate, ethylene glycol monohexyl ether, ethylene glycol mono-2-ethylhexyl ether, ethylene glycol monophenyl ether, ethylene glycol monobenzyl ether, diethylene glycol monoethyl ether, diethylene glycol monoisopropyl ether, diethylene glycol mono-n-butyl ether, diethylene glycol monoisobutyl ether, diethylene glycol monohexyl ether, diethylene glycol monophenyl ether, diethylene glycol monobenzyl ether, diethylene glycol diethyl ether, diethylene glycol dibutyl ether, diethylene glycol butylmethyl ether, triethylene glycol dimethyl ether, triethylene glycol monomethyl ether, triethylene glycol-n-butyl ether, triethylene glycol butylmethyl ether, tetraethylene glycol dimethyl ether, dipropylene glycol monomethyl ether, dipropylene glycol mono-n-propyl ether, dipropylene glycol mono-n-butyl ether, tripropylene glycol dimethyl ether, tripropylene glycol monomethyl ether, tripropylene glycol mono-n-propyl ether, tripropylene glycol mono-n-butyl ether, ethylene glycol monoethyl ether acetate, ethylene glycol monobutyl ether acetate, diethylene glycol monomethyl ether acetate, diethylene glycol monoethyl ether acetate, diethylene glycol monobutyl ether acetate, triacetin, propylene glycol diacetate, dipropylene glycol methyl-n-propyl ether, dipropylene glycol methyl ether acetate, 1,4-butanediol diacetate, 1,3-butylene glycol diacetate, 1,6-hexanediol diacetate, triethylene glycol diacetate, γ-butyrolactone, methyl benzoate, ethyl benzoate, propyl benzoate, butyl benzoate, dihexyl malonate, diethyl succinate, dipropyl succinate, dibutyl succinate, dihexyl succinate, dimethyl adipate, diethyl adipate, dibutyl adipate, etc. These may be used singly or in mixture thereof.

The organic solvent(s) having a boiling point of 180° C. or higher may be appropriately selected, for example, from the above list according to the temperature at which the inventive resist underlayer film material is heated, etc. The boiling point of the organic solvent(s) having a boiling point of 180° C. or higher is preferably 180° C. to 300° C., further preferably 200° C. to 300° C. Such boiling points presumably prevent the evaporation rate at baking (heating) from becoming excessive, which would otherwise occur if the boiling point is too low. Thus, the boiling points can provide sufficient thermal flowability during the film formation, and a resist underlayer film excellent in filling property and planarizing property can be formed. Moreover, such boiling points are not too high, so that the high-boiling-point solvent(s) evaporate after baking and do not remain in the film; thus, the boiling points do not adversely affect the film physical properties, such as etching resistance.

Moreover, when the organic solvent(s) having a boiling point of 180° C. or higher are used, the organic solvent(s) are blended in an amount of preferably 1 to 30 parts by mass based on 100 parts by mass of the organic solvent (s) having a boiling point of lower than 180° C. Such a formulation amount prevents a failure in providing sufficient thermal flowability during baking, which would otherwise occur if the formulation amount is too small. In addition, degradation of the film physical properties such as etching resistance is prevented, which would otherwise occur if the formulation amount is so large that the solvent(s) remain in the film. Thus, such a formulation amount is preferable.

In the inventive resist underlayer film material, an acid generator (C) can be added so as to further promote the curing reaction. The acid generator includes a material that generates an acid by thermal decomposition, and a material that generates an acid by light irradiation. Any of these can be added. Specifically, materials disclosed in paragraphs [0061] to [0085] of JP 2007-199653 A can be added, but the present invention is not limited thereto.

One kind of the acid generator can be used singly, or two or more kinds thereof can be used in combination. When an acid generator is added, the acid generator is added in an amount of preferably 0.05 to 50 parts by mass, more preferably 0.1 to 10 parts by mass, based on 100 parts by mass of the compound shown by the general formula (1).

To the inventive resist underlayer film material, a surfactant (D) can be added so as to enhance the coating property in spin coating. As the surfactant, for example, those disclosed in [0142] to [0147] of JP 2009-269953 A can be used.

When a surfactant is added, the surfactant is added in an amount of preferably 0.001 to 20 parts by mass, more preferably 0.01 to 10 parts by mass, based on 100 parts by mass of the compound shown by the general formula (1).

Moreover, to the inventive resist underlayer film material, a crosslinking agent (E) can also be added so as to increase the curability and to further suppress intermixing with an upper layer film. The crosslinking agent is not particularly limited, and known various types of crosslinking agents can be widely used. Examples thereof can include melamine-based crosslinking agents, glycoluril-based crosslinking agents, benzoguanamine-based crosslinking agents, urea-based crosslinking agents, β-hydroxyalkylamide-based crosslinking agents, isocyanurate-based crosslinking agents, aziridine-based crosslinking agents, oxazoline-based crosslinking agents, epoxy-based crosslinking agents, and phenol-based crosslinking agents. When a crosslinking agent is added, the crosslinking agent is added in an amount of preferably 1 to 50 parts by mass, more preferably 10 to 40 parts by mass, based on 100 parts by mass of the compound shown by the general formula (1).

Specific examples of the melamine-based crosslinking agents include hexamethoxymethylated melamine, hexabutoxymethylated melamine, alkoxy- and/or hydroxy-substituted derivatives thereof, and partial self-condensates thereof. Specific examples of the glycoluril-based crosslinking agents include tetramethoxymethylated glycoluril, tetrabutoxymethylated glycoluril, alkoxy- and/or hydroxy-substituted derivatives thereof, and partial self-condensates thereof. Specific examples of the benzoguanamine-based crosslinking agents include tetramethoxymethylated benzoguanamine, tetrabutoxymethylated benzoguanamine, alkoxy- and/or hydroxy-substituted derivatives thereof, and partial self-condensates thereof. Specific examples of the urea-based crosslinking agents include dimethoxymethylated dimethoxyethyleneurea, alkoxy- and/or hydroxy-substituted derivatives thereof, and partial self-condensates thereof. A specific example of the β-hydroxyalkylamide-based crosslinking agents includes N,N,N',N'-tetra(2-hydroxyethyl)adipic acid amide. Specific examples of the isocyanurate-based crosslinking agents include triglycidyl isocyanurate and triallyl isocyanurate. Specific examples of the aziridine-based crosslinking agents include 4,4'-bis(ethyleneiminocarbonylamino)diphenylmethane and 2,2-bishydroxymethylbutanol-tris[3-(1-aziridinyl)propionate]. Specific examples of the oxazoline-based crosslinking agents include 2,2'-isopropylidene bis(4-benzyl-2-oxazoline), 2,2'-isopropylidene bis(4-phenyl-2-oxazoline), 2,2'-methylenebis4,5-diphenyl-2-oxazoline, 2,2'-methylenebis-4-phenyl-2-oxazoline, 2,2'-methylenebis-4-tert-butyl-2-oxazoline, 2,2'-bis(2-oxazoline), 1,3-phenylenebis(2-oxazoline), 1,4-phenylenebis(2-oxazoline), and a 2-isopropenyloxazoline copolymer. Specific examples of the epoxy-based crosslinking agents include diglycidyl ether, ethylene glycol diglycidyl ether, 1,4-butanediol diglycidyl ether, 1,4-cyclohexanedimethanol diglycidyl ether, poly(glycidyl methacrylate), trimethylolethane triglycidyl ether, trimethylolpropane triglycidyl ether, and pentaerythritol tetraglycidyl ether.

As the phenol-based crosslinking agents that can be added, known various crosslinking agents can be widely used. Specifically, a compound shown by the following general formula (7) is particularly preferable.

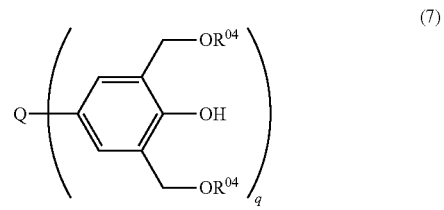

In the formula, Q represents a single bond, or a hydrocarbon group with a valency of "q" having 1 to 20 carbon atoms. $R^{04}$ represents a hydrogen atom, or an alkyl group having 1 to 20 carbon atoms. "q" represents an integer of 1 to 5.

Q is a single bond, or a hydrocarbon group with a valency of "q" having 1 to 20 carbon atoms. "q" is an integer of 1 to 5, more preferably 2 or 3. In the case where Q is a hydrocarbon group with a valency of "q" having 1 to 20 carbon atoms, Q is a hydrocarbon group having a valency of "q" and corresponds to a hydrocarbon having 1 to 20 carbon atoms but excluding "q" hydrogen atoms therefrom. More specific examples of the hydrocarbon having 1 to 20 carbon atoms can include methane, ethane, propane, butane, isobutane, pentane, cyclopentane, hexane, cyclohexane, methylpentane, methylcyclohexane, dimethylcyclohexane, trimethylcyclohexane, benzene, toluene, xylene, ethylbenzene, ethylisopropylbenzene, diisopropylbenzene, methylnaphthalene, ethylnaphthalene, and eicosane. $R^{04}$ is a hydrogen atom or an alkyl group having 1 to 20 carbon atoms. Specific examples of the alkyl group having 1 to 20 carbon atoms can include a methyl group, an ethyl group, a propyl group, an isopropyl group, a butyl group, an isobutyl group, a pentyl group, an isopentyl group, a hexyl group, an octyl group, an ethylhexyl group, a decyl group, and an eicosanyl group.

The compound shown by the general formula (7) is preferably blended to the inventive resist underlayer film material because the film thickness uniformity is enhanced in some cases in addition to the effect of increasing the curability of the resist underlayer film.

Specific examples of the compound shown by the general formula (7) can include, but are not limited to, the following compounds. In the following formulae, $R^{04}$ is as defined above.

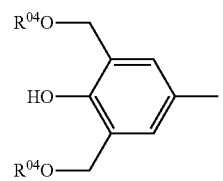

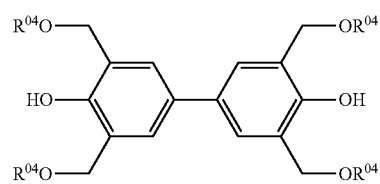

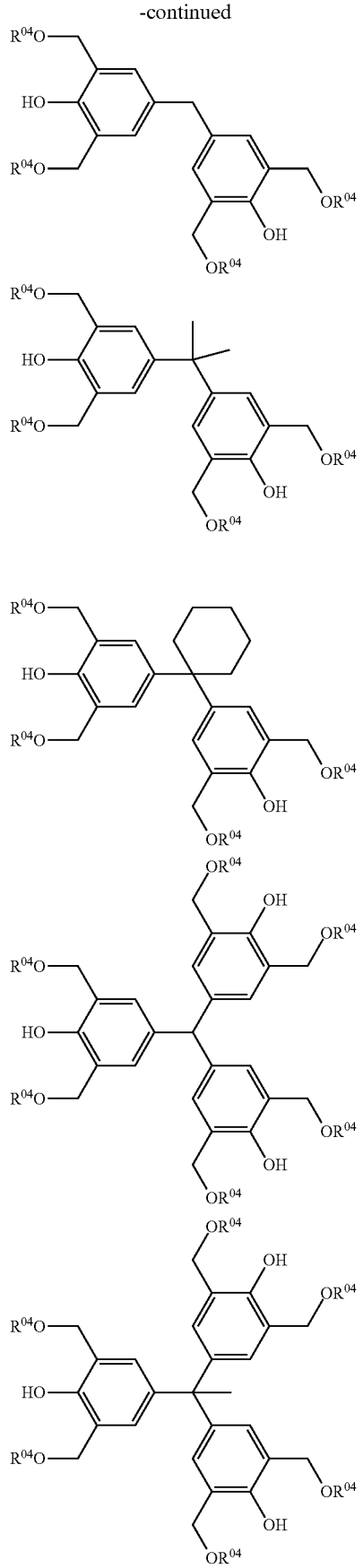
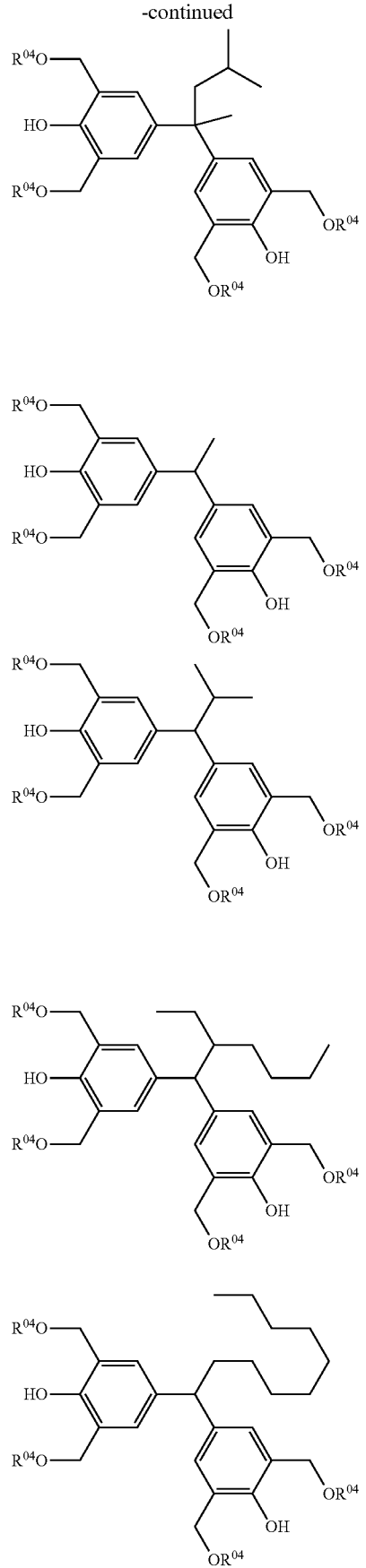

39
-continued
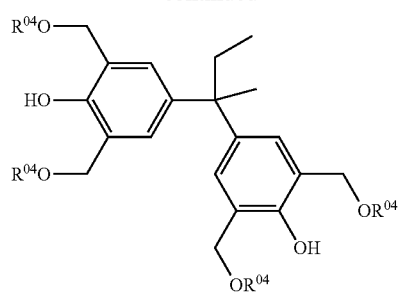
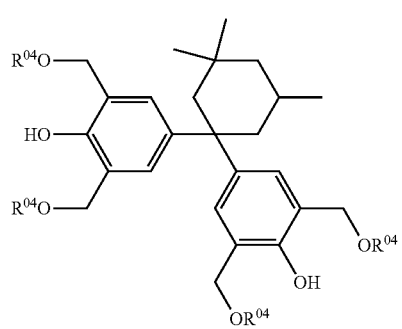
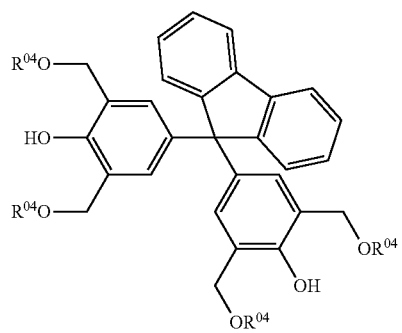
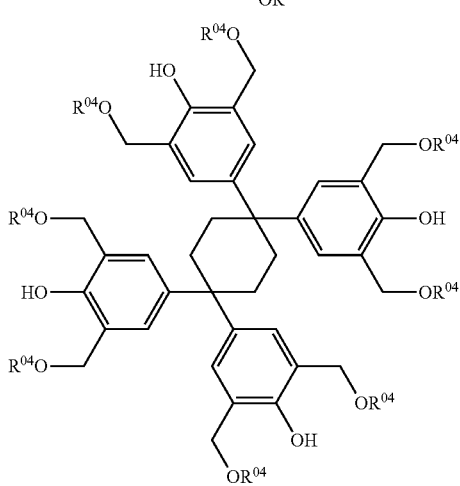
40
-continued
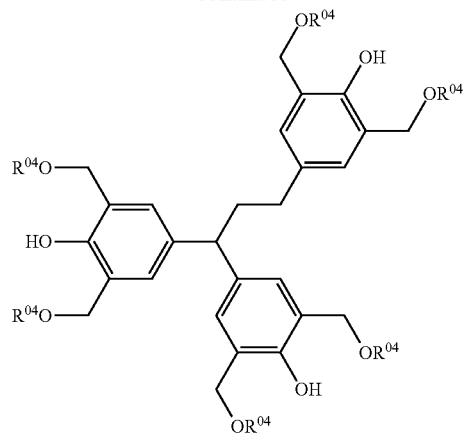
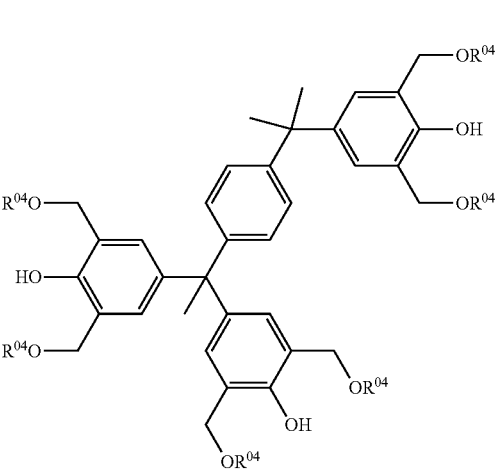
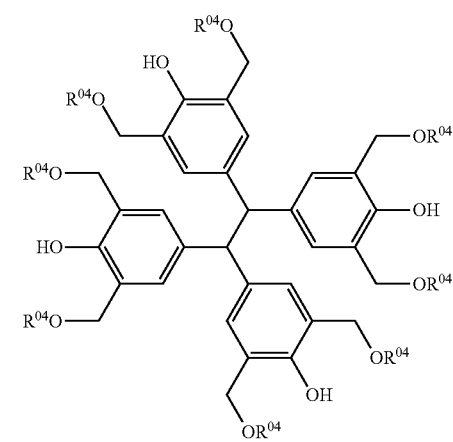

-continued

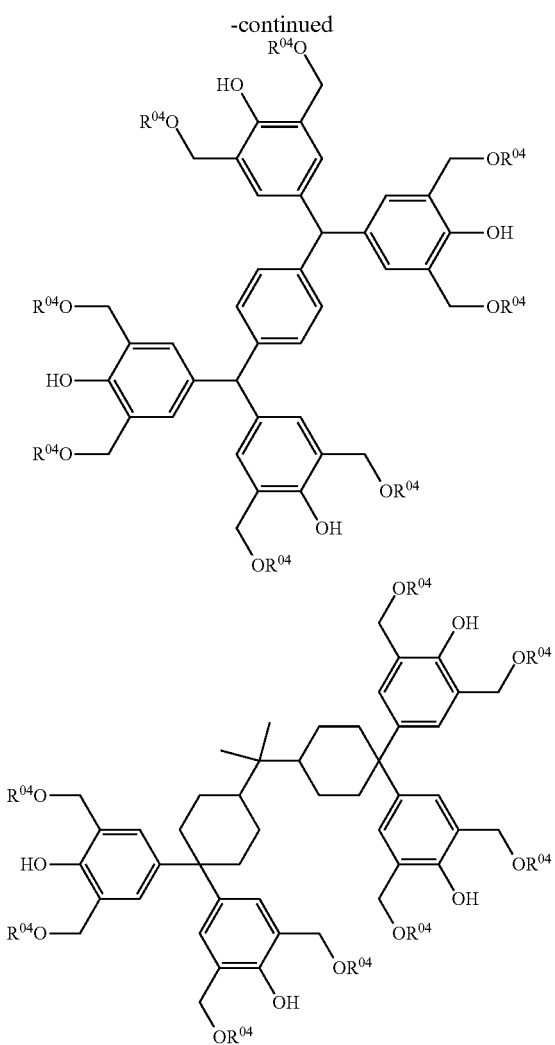

Further, to the inventive resist underlayer film material, a plasticizer (F) can be added so as to further enhance planarizing and filling properties. The plasticizer is not particularly limited, and known various types of plasticizers can be widely used. Examples thereof can include low-molecular-weight compounds, such as phthalic acid esters, adipic acid esters, phosphoric acid esters, trimellitic acid esters, and citric acid esters; and polymers, such as polyethers, polyesters, and polyacetal-based polymers disclosed in JP 2013-253227 A. When a plasticizer is added, the plasticizer is added in an amount of preferably 5 to 500 parts by mass, more preferably 10 to 200 parts by mass, based on 100 parts by mass of the compound shown by the general formula (1).

Furthermore, to the inventive resist underlayer film material, a pigment (G) can be added so as to further enhance the resolution in multilayer lithography patterning. The pigment is not particularly limited, as long as the compound has appropriate absorption at exposure wavelength, and known various compounds can be widely used. Examples thereof can include benzenes, naphthalenes, anthracenes, phenanthrenes, pyrenes, isocyanuric acids, and triazines. When a pigment is added, the pigment is added in an amount of preferably 0.01 to 10 parts by mass, more preferably 0.1 to 5 parts by mass, based on 100 parts by mass of the compound shown by the general formula (1).

<Patterning Processes>

Moreover, the present invention provides a patterning process for forming a pattern in a substrate to be processed, the process including steps of:
- (I-1) applying the above-described resist underlayer film material onto a substrate to be processed, followed by heating to form a resist underlayer film;
- (I-2) forming a resist upper layer film on the resist underlayer film by using a photoresist material;
- (I-3) subjecting the resist upper layer film to pattern exposure and then development with a developer to form a pattern in the resist upper layer film;
- (I-4) transferring the pattern to the resist underlayer film by dry etching while using the resist upper layer film having the formed pattern as a mask; and
- (I-5) processing the substrate to be processed while using the resist underlayer film having the formed pattern as a mask to form the pattern in the substrate to be processed (2-layer resist process).

Further, the present invention provides a patterning process for forming a pattern in a substrate to be processed, the process including steps of:
- (II-1) applying the above-described resist underlayer film material onto a substrate to be processed, followed by heating to form a resist underlayer film;
- (II-2) forming a resist middle layer film on the resist underlayer film;
- (II-3) forming a resist upper layer film on the resist middle layer film by using a photoresist material;
- (II-4) subjecting the resist upper layer film to pattern exposure and then development with a developer to form a pattern in the resist upper layer film;
- (II-5) transferring the pattern to the resist middle layer film by dry etching while using the resist upper layer film having the formed pattern as a mask;
- (II-6) transferring the pattern to the resist underlayer film by dry etching while using the resist middle layer film having the transferred pattern as a mask; and
- (II-7) processing the substrate to be processed while using the resist underlayer film having the formed pattern as a mask to form the pattern in the substrate to be processed (3-layer resist process).

In addition, the present invention provides a patterning process for forming a pattern in a substrate to be processed, the process including steps of:
- (III-1) applying the above-described resist underlayer film material onto a substrate to be processed, followed by heating to form a resist underlayer film;
- (III-2) forming an inorganic hard mask middle layer film selected from a silicon oxide film, a silicon nitride film, and a silicon oxynitride film on the resist underlayer film;
- (III-3) forming an organic thin film on the inorganic hard mask middle layer film;
- (III-4) forming a resist upper layer film on the organic thin film by using a photoresist material;
- (III-5) subjecting the resist upper layer film to pattern exposure and then development with a developer to form a pattern in the resist upper layer film;
- (III-6) transferring the pattern to the organic thin film and the inorganic hard mask middle layer film by dry etching while using the resist upper layer film having the formed pattern as a mask;
- (III-7) transferring the pattern to the resist underlayer film by dry etching while using the inorganic hard mask middle layer film having the transferred pattern as a mask; and (III-8) processing the substrate to be processed while using the resist underlayer film having the formed pattern as a mask to form the pattern in the substrate to be processed (4-layer resist process).

The thickness of the resist underlayer film utilized in the present invention is appropriately selected, and is preferably 2 to 20,000 nm, particularly preferably 50 to 15,000 nm. When the resist underlayer film is used for 3-layer process, a resist middle layer film containing silicon and a resist upper layer film containing no silicon can be formed thereon. When the resist underlayer film is used for 2-layer process, a resist upper layer film containing silicon or a resist upper layer film containing no silicon can be formed thereon.

The patterning processes according to the present invention are suitably employed in multilayer resist processes: silicon-involving 2-layer resist process; 3-layer resist process using a silicon-containing middle layer film; 4-layer resist process using a silicon-containing middle layer film and an organic thin film; or silicon-free 2-layer resist process.

[3-Layer Resist Process]

Hereinbelow, the inventive patterning processes will be described by illustrating a 3-layer resist process as an example, but are not limited to this process. In this case, the above-described resist underlayer film material is used to form a resist underlayer film on a substrate. On the resist underlayer film, a resist middle layer film is formed using a resist middle layer film material containing silicon atoms. On the resist middle layer film, a resist upper layer film is formed using a resist upper layer film material as a photoresist composition, so that a multilayer resist film is formed. A pattern circuit region of the resist upper layer film is subjected to exposure and development with a developer to form a resist pattern in the resist upper layer film. Using the pattern-formed resist upper layer film as a mask, the resist middle layer film is etched. Using the pattern-formed resist middle layer film as a mask, the resist underlayer film is etched. Further, using the pattern-formed resist underlayer film as a mask, the substrate is processed. In this manner, the pattern can be formed in the substrate.

The resist middle layer film containing silicon atoms exhibits resistance to etching with an oxygen gas or a hydrogen gas. Thus, when the resist underlayer film is etched as described above using the resist middle layer film as the mask, an etching gas mainly containing an oxygen gas or a hydrogen gas is preferably used for the etching.

Moreover, according to the inventive patterning process, a pattern can be formed in a substrate as follows. Specifically, at least, a substrate is prepared to have: a resist underlayer film formed thereon by using the above-described resist underlayer film material; an inorganic hard mask middle layer film selected from a silicon oxide film, a silicon nitride film, and a silicon oxynitride film, and formed on the resist underlayer film; and a resist upper layer film formed on the inorganic hard mask middle layer film by using a resist upper layer film material as a photoresist composition. A pattern circuit region of the resist upper layer film is subjected to exposure and development with a developer to form a resist pattern in the resist upper layer film. Using the obtained resist pattern as an etching mask, the inorganic hard mask middle layer film is etched. Using the resulting inorganic hard mask middle layer film pattern as an etching mask, the resist underlayer film is etched. Using the resulting resist underlayer film pattern as a mask, the substrate is processed to thus pattern the substrate.

In the case where an inorganic hard mask middle layer film is formed on the resist underlayer film as described above, a silicon oxide film, a silicon nitride film, and a silicon oxynitride film (SiON film) can be formed by a CVD method, an ALD method, or the like. The method for forming the nitride film is disclosed in JP 2002-334869 A and WO 2004/066377 A1. The film thickness of the inorganic hard mask is preferably 5 to 200 nm, more preferably 10 to 100 nm. Above all, a SiON film is the most effective as an antireflective coating and is most preferably used in ArF exposure application.

As the silicon-containing resist middle layer film in the 3-layer resist process, a polysilsesquioxane-based middle layer film can be used suitably. The polysilsesquioxane-based middle layer film is readily provided with an antireflective effect in excimer exposure. Thereby, there are such advantages of satisfactorily suppressing reflection light in pattern exposure of the resist upper layer film, and achieving excellent resolution. Particularly, for 193-nm light exposure, if a material containing many aromatic groups is used as a resist underlayer film, the k-value and thus the substrate reflection are increased. However, the reflection can be suppressed by the resist middle layer film, and so the substrate reflection can be reduced to 0.5% or less. As the resist middle layer film having the antireflective effect, a polysilsesquioxane is preferably used, the polysilsesquioxane having anthracene for 248-nm and 157-nm light exposure, or a phenyl group or a light-absorbing group having a silicon-silicon bond for 193-nm light exposure in a pendant structure, and being crosslinked by an acid or heat.

In this case, forming a silicon-containing resist middle layer film by a spin-coating method is simpler and more advantageous regarding cost than a CVD method.

The resist upper layer film in the 3-layer resist film may be a positive type or a negative type, and any generally-used photoresist composition can be employed. When the resist upper layer film is formed from the photoresist composition, a spin-coating method is preferably employed as in the case of forming the resist underlayer film. After spin-coating of the photoresist composition, pre-baking is preferably performed at 60 to 180° C. for 10 to 300 seconds. Then, light exposure, post-exposure bake (PEB), and development are performed according to conventional methods to obtain the resist pattern. Note that the thickness of the resist upper layer film is not particularly limited, but is preferably 30 to 500 nm, and 50 to 400 nm is particularly preferable.

Additionally, examples of exposure light can include a high-energy beam with a wavelength of 300 nm or less, specifically, excimer laser of 248 nm, 193 nm, and 157 nm, soft X-ray of 3 to 20 nm, electron beam, X-ray, etc.

Next, etching is performed using the obtained resist pattern as a mask. In the 3-layer process, the resist middle layer film can be etched using a fluorocarbon-based gas and using the resist pattern as the mask. Then, the resist underlayer film is etched using an oxygen gas or a hydrogen gas and using the resist middle layer film pattern as the mask.

Subsequently, the substrate to be processed can be etched according to a conventional method. For example, the substrate made of $SiO_2$, SiN, or silica-based low-dielectric insulating film is etched mainly with a fluorocarbon-based gas; and p-Si, Al, or W is etched mainly with a chlorine- or bromine-based gas. When the substrate is processed by etching with a fluorocarbon-based gas, the silicon-containing middle layer in the 3-layer process is removed when the substrate is processed. When the substrate is etched with a chlorine- or bromine-based gas, the silicon-containing middle layer needs to be removed by, for example, additional dry etching with a fluorocarbon-based gas after the substrate processing.

Note that as the substrate to be processed, a layer to be processed may be formed on a substrate. The substrate is not particularly limited, and examples thereof include substrates made of Si, α-Si, p-Si, $SiO_2$, SiN, SiON, W, TiN, Al, or the like. However, the material different from that of the layer to be processed is selected. Examples of the layer to be processed include: various Low-k films made of Si, $SiO_2$, SiON, SiN, p-Si, α-Si, W, TiN, W—Si, Al, Cu, Al—Si, or the like; and stopper films thereof. The layer is formed to have a thickness of generally 50 to 10,000 nm, in particular, 100 to 5,000 nm.

The inventive patterning processes are suitable for processing a stepped substrate having a structure or step with a height of 30 nm or more. On such a stepped substrate, the inventive resist underlayer film is formed to fill and planarize the substrate. This enables the resist middle layer film and the resist upper layer film formed thereafter to have uniform film thicknesses. Thus, exposure depth margin (depth of focus: DOF) in photolithography is readily secured and very preferable.

Hereinbelow, an example of the 3-layer resist process will be specifically described with reference to FIG. 1. As shown in FIG. 1 (A), in the 3-layer resist process, a resist underlayer film 3 is formed on a layer 2 to be processed that has been stacked on a substrate 1. Then, a resist middle layer film 4 is formed, and a resist upper layer film 5 is formed thereon.

Next, as shown in FIG. 1 (B), a predetermined portion 6 of the resist upper layer film is exposed to light, followed by PEB (baking after exposure) and development to form a resist upper layer film pattern 5a (FIG. 1 (C)). While using the obtained resist upper layer film pattern 5a as a mask, the resist middle layer film 4 is etched with a CF-based gas. Thereby, a resist middle layer film pattern 4a is formed (FIG. 1 (D)). After the resist upper layer film pattern 5a is removed, the resist underlayer film 3 is etched with oxygen or hydrogen plasma while using the obtained resist middle layer film pattern 4a as a mask. Thereby, a resist underlayer film pattern 3a is formed (FIG. 1 (E)). Further, after the resist middle layer film pattern 4a is removed, the layer 2 to be processed is etched while using the resist underlayer film pattern 3a as a mask. Thus, a pattern 2a is formed (FIG. 1 (F)).

When an inorganic hard mask middle layer film is used, the resist middle layer film 4 is the inorganic hard mask middle layer film, and when an organic thin film is formed, the organic thin film layer is disposed between the resist middle layer film 4 and resist upper layer film 5. The etching of the organic thin film may be performed continuously before the etching of the resist middle layer film 4. Alternatively, after the organic thin film is etched alone, the etching apparatus is changed, for example, and then the resist middle layer film 4 may be etched.

[4-Layer Resist Process]

Furthermore, the present invention is suitably applicable to a 4-layer resist process using an organic thin film. In this case, at least, a substrate is prepared to have: a resist underlayer film formed thereon by using the above-described resist underlayer film material; an inorganic hard mask middle layer film selected from a silicon oxide film, a silicon nitride film, and a silicon oxynitride film, and formed on the resist underlayer film; an organic thin film formed on the inorganic hard mask middle layer film; and a resist upper layer film formed on the organic thin film by using a resist upper layer film material as a photoresist composition. A pattern circuit region of the resist upper layer film is subjected to exposure and development with a developer to form a resist pattern in the resist upper layer film. Using the obtained resist pattern as an etching mask, the organic thin film and the inorganic hard mask middle layer film are etched. Using the resulting inorganic hard mask middle layer film pattern as an etching mask, the resist underlayer film is etched. Using the resulting resist underlayer film pattern as a mask, the substrate is processed, so that the pattern can be formed in the substrate.

On the resist middle layer film, a photoresist film may be formed as the resist upper layer film. Alternatively, after an organic thin film is formed on the resist middle layer film as described above by spin coating, the photoresist film may be formed on the organic thin film. When a SiON film is used as the resist middle layer film and an organic antireflective coating (BARC) having a light-absorbing group at the exposure wavelength is used as the organic thin film, the two layers of antireflective coating including the SiON film and the organic thin film in excimer exposure make it possible to suppress the reflection even in liquid immersion exposure at a high NA exceeding 1.0. Another advantage in forming the organic thin film is having an effect of reducing footing of the photoresist pattern immediately above the SiON film. Moreover, when an adhesion film (ADL) having excellent affinity to the upper layer photoresist is used as the organic thin film, there is also such an advantage that pattern collapse of the photoresist can be suppressed.

<Methods for Forming Resist Underlayer Film>

The present invention provides a method for forming a resist underlayer film that serves as an organic planarizing film employed in a semiconductor device manufacturing process, the method including:

spin-coating a substrate to be processed with the above-described resist underlayer film material; and heating the substrate coated with the resist underlayer film material at a temperature of 100° C. or higher and 600° C. or lower for 10 to 600 seconds to form a cured film.

The present invention also provides a method for forming a resist underlayer film that serves as an organic planarizing film employed in a semiconductor device manufacturing process, the method including:

spin-coating a substrate to be processed with the above-described resist underlayer film material; and heating the substrate coated with the resist underlayer film material under an atmosphere with an oxygen concentration of 1% or more and 21% or less to form a cured film.

Alternatively, the present invention provides a method for forming a resist underlayer film that serves as an organic planarizing film employed in a semiconductor device manufacturing process, the method including:

spin-coating a substrate to be processed with the above-described resist underlayer film material; and heating the substrate coated with the resist underlayer film material under an atmosphere with an oxygen concentration of less than 1% to form a cured film.

In the inventive methods for forming a resist underlayer film, a substrate to be processed is coated with the above-described resist underlayer film material by a spin-coating method etc. By employing a method like spin-coating method, favorable filling property can be obtained. After the spin-coating, baking (heating) is performed to evaporate the solvent and to promote the crosslinking reaction, thereby preventing the mixing with a resist upper layer film or a resist middle layer film. The baking can be performed in a temperature range of 100° C. or higher to 600° C. or lower, preferably 100° C. or higher to 300° C. or lower, more preferably 150° C. or higher to 280° C. or lower. The baking time is in a range of, for example, 10 seconds to 600 seconds, preferably 10 to 300 seconds. Appropriately adjusting the baking temperature and time within the above ranges can make planarizing, filling, and curing properties suitable for use. With the baking temperature at 100° C. or higher, curing proceeds sufficiently, preventing mixing with an upper layer film or middle layer film. With the baking temperature at 600° C. or lower, not only thermal decomposition of the base resin but also the film thickness reduction can be suppressed, and the film surface becomes more uniform.

As the atmosphere during baking, any of oxygen-containing atmosphere (oxygen concentration: 1% to 21%), as in air, and oxygen-free atmosphere, as in nitrogen, can be selected as necessary. For example, if a substrate to be processed is susceptible to oxidation in air, the substrate damage can be suppress by forming a cured film through heating under an atmosphere with an oxygen concentration of less than 1%.

Moreover, in the inventive methods for forming a resist underlayer film, a substrate having a structure or step with a height of 30 nm or more is preferably used as the substrate to be processed. The inventive methods for forming a resist underlayer film are particularly useful when a void-free planarizing organic film is formed particularly on a substrate having a structure or step with a height of 30 nm or more.

EXAMPLE

Hereinafter, the present invention will be specifically described with reference to Examples and Comparative Examples. However, the present invention is not limited to these descriptions. Note that molecular weight and dispersity were measured by the following methods. Weight-average molecular weight (Mw) and dispersity (Mw/Mn) were determined in terms of polystyrene by gel permeation chromatography (GPC) using tetrahydrofuran as an eluent.

[Synthesis Example 1] Synthesis of Compound (A1)

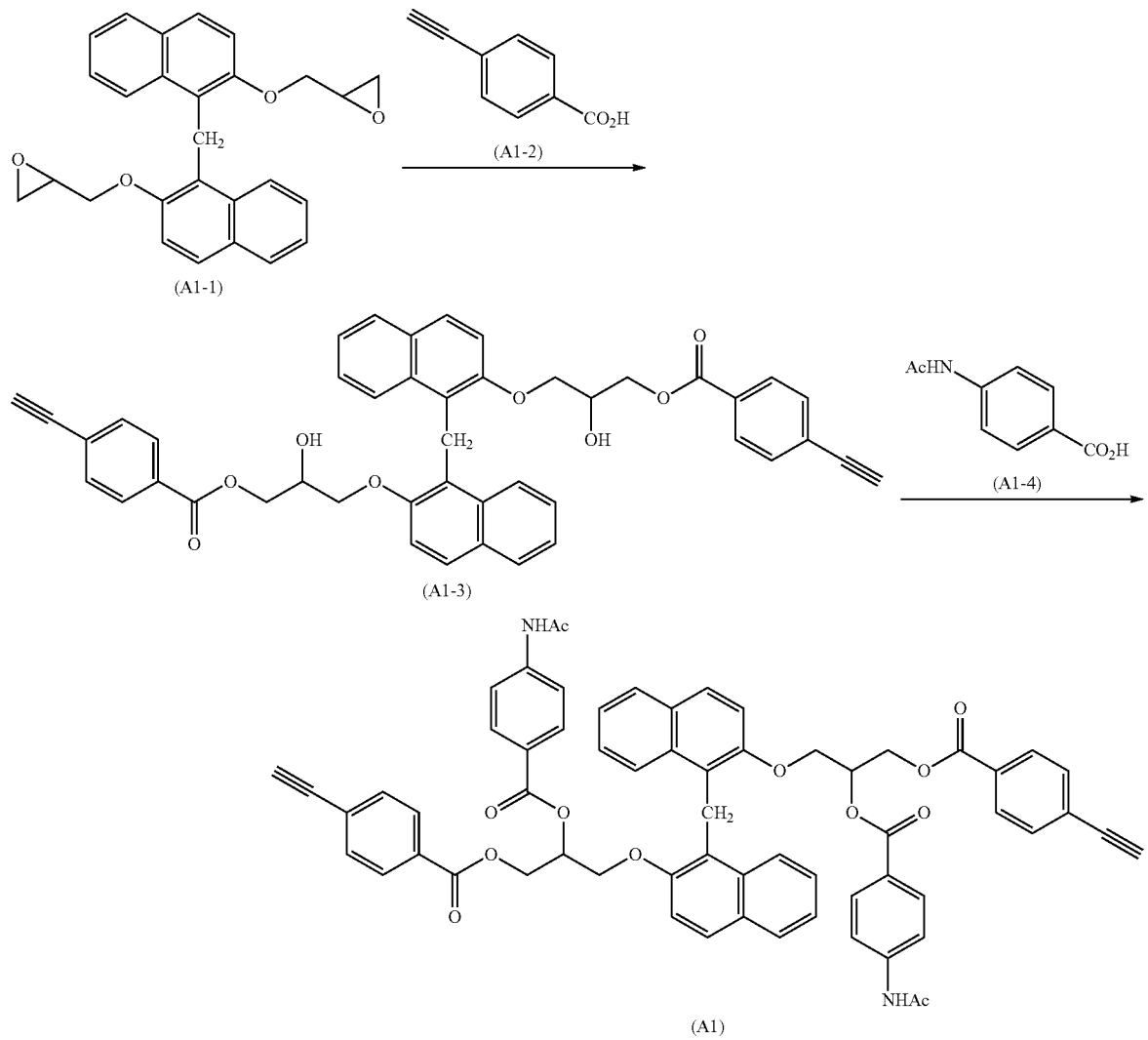

A mixture containing 41.2 g of an epoxide (A1-1), 29.2 g of an organic acid (A1-2), 1.1 g of benzyltriethylammonium chloride, 210 g of N, N-dimethylformamide (hereinafter, DMF), and 70 g of propylene glycol monomethyl ether (hereinafter, PGME) was heated and stirred under nitrogen atmosphere at 100° C. for 16 hours. The PGME was distilled off by condensation under reduced pressure. Thereby, a DMF solution of an intermediate (A1-3) was obtained.

To this, 39.4 g of a carboxylic acid (A1-4), 42.2 g of 1-(3-dimethylaminopropyl)-3-ethylcarbodiimide hydrochloride, and 26.9 g of 4-dimethylaminopyridine were added, and heated and stirred under nitrogen atmosphere at 50° C. for 16 hours. To the reaction solution, 4-methyl-2-pentanone was added for dilution, followed by general aqueous work-up. After propylene glycol monomethyl ether acetate (hereinafter, PGMEA) was added, the 4-methyl-2-pentanone was distilled off by condensation under reduced pressure. Then, PGMEA was added to adjust the concentration. Thus, a 20 mass % solution of a target product (A1) in PGMEA was obtained. GPC molecular weight: 1420, dispersity: 1.24.

[Synthesis Examples 2 to 8, Comparative Synthesis Examples 1 to 8] Synthesis of Compounds (A2) to (A8) and Comparative Compounds (R1) to (R8)

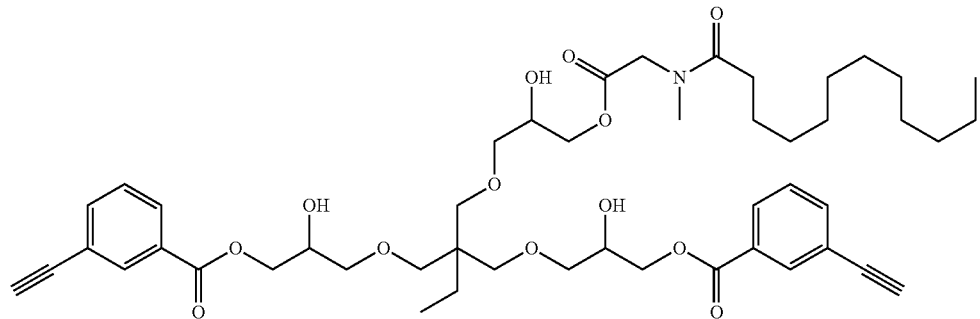

(A2)

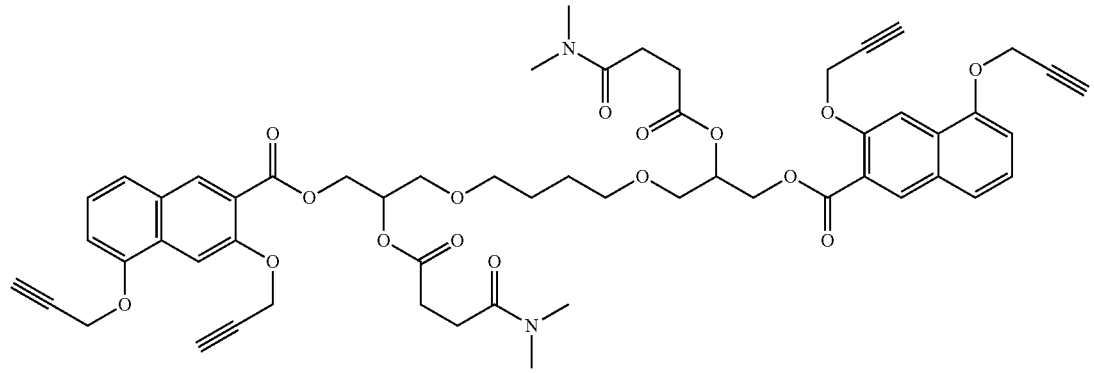

(A3)

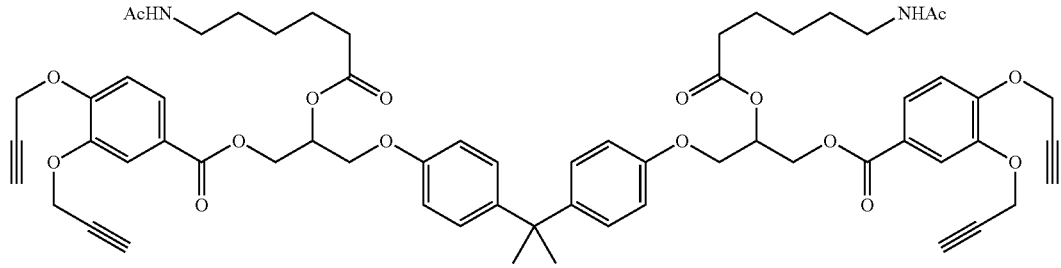

(A4)

-continued
(A5)
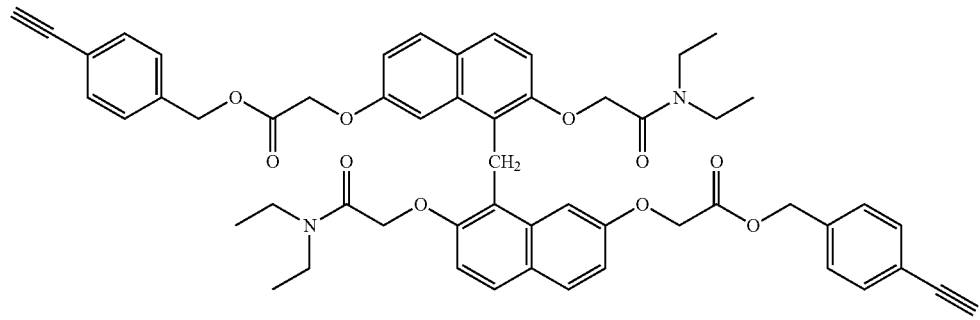
(A6)
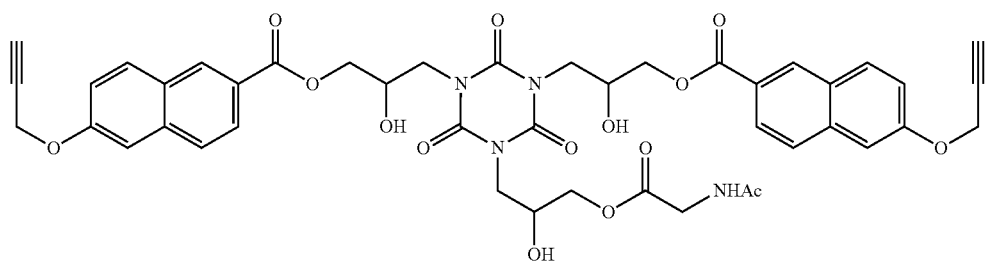
(A7)
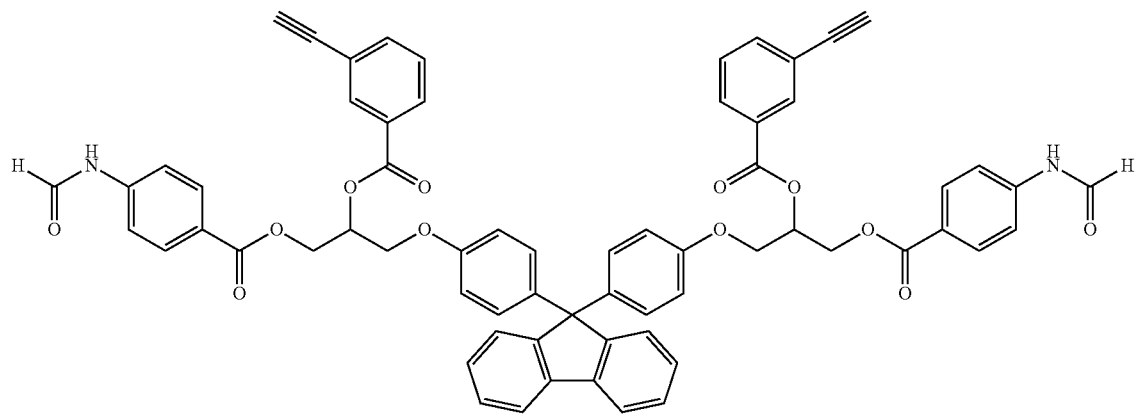
(A8)
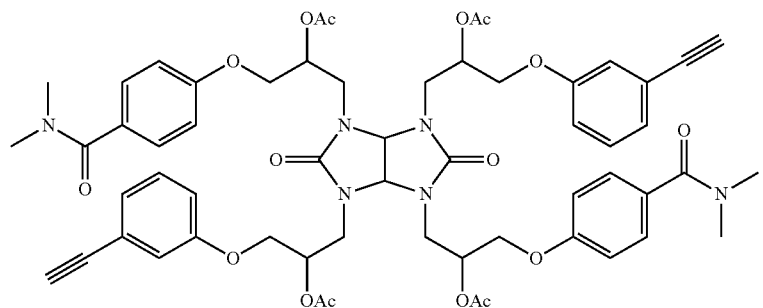
(R1)
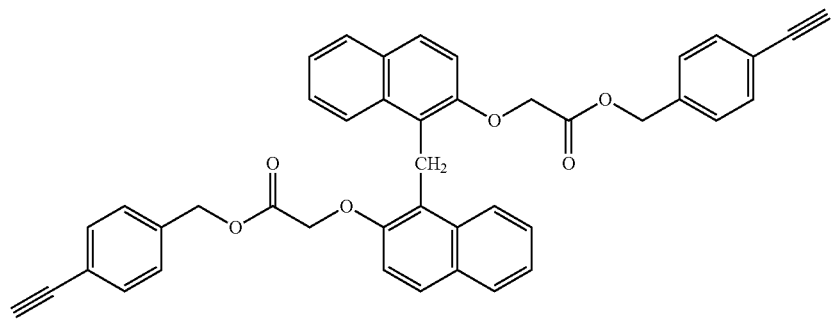

-continued
(R2)
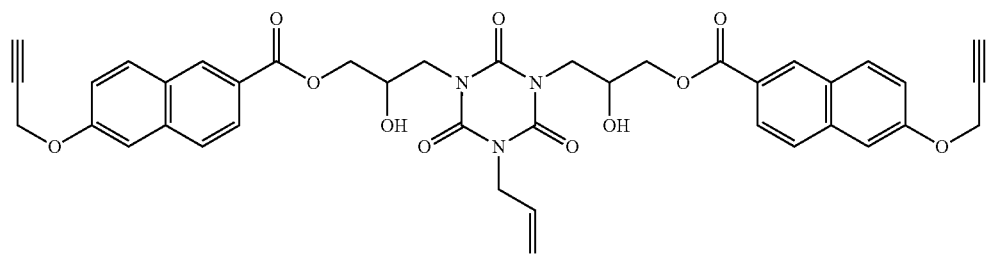
(R3)
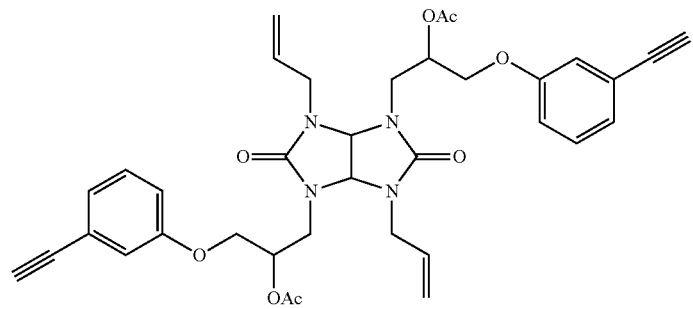
(R4)
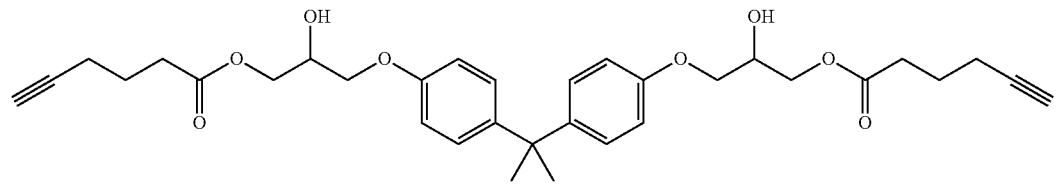
(R5)
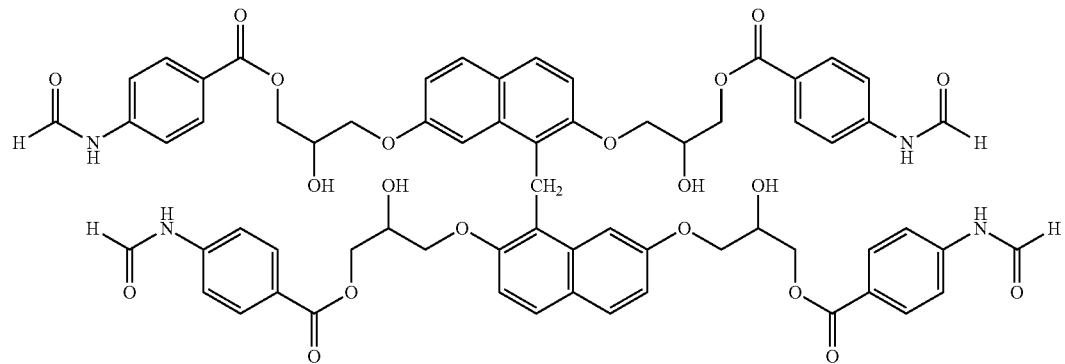
(R6)
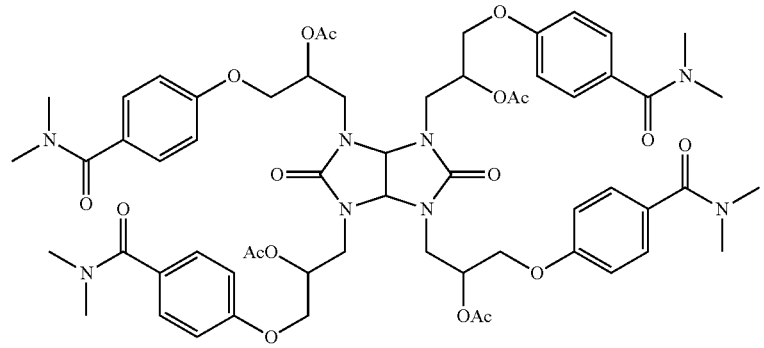

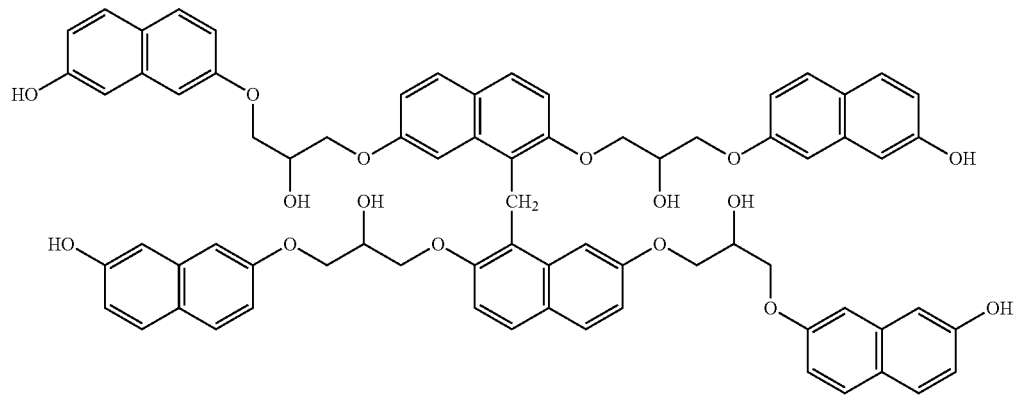
(R7)

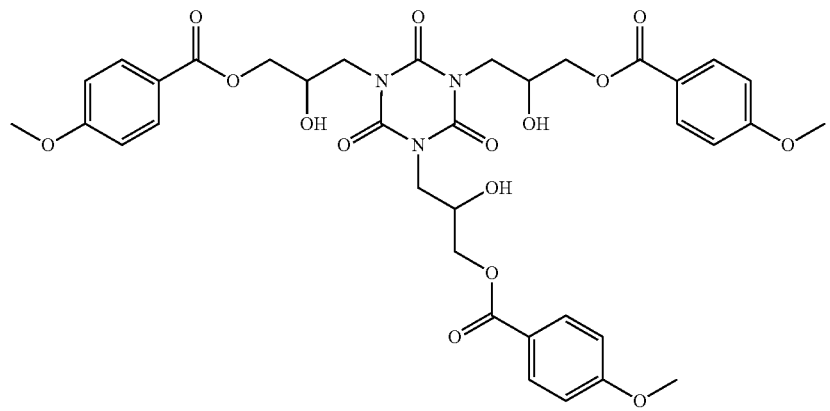
(R8)

Compounds (A2) to (A8) and Comparative Compounds (R1) to (R8) were obtained as 20 mass % solutions in PGMEA by the method according to [Synthesis Example 1], except that the kinds and the amounts of raw materials were changed depending on the structure of each compound. Table 1 shows the measured weight-average molecular weight (Mw) and dispersity (Mw/Mn) of these compounds.

TABLE 1

| Synthesis Example | Compound | Mw (GPC) | Mw/Mn (GPC) |
|---|---|---|---|
| 1 | A1 | 1420 | 1.24 |
| 2 | A2 | 1080 | 1.04 |
| 3 | A3 | 1170 | 1.05 |
| 4 | A4 | 1270 | 1.06 |
| 5 | A5 | 1090 | 1.12 |
| 6 | A6 | 1100 | 1.04 |
| 7 | A7 | 1350 | 1.07 |
| 8 | A8 | 1280 | 1.05 |
| 9 | R1 | 1250 | 1.15 |
| 10 | R2 | 1050 | 1.04 |
| 11 | R3 | 1100 | 1.05 |
| 12 | R4 | 1080 | 1.04 |
| 13 | R5 | 1420 | 1.22 |
| 14 | R6 | 1130 | 1.05 |
| 15 | R7 | 1610 | 1.31 |
| 16 | R8 | 1070 | 1.06 |

Preparation of Resist Underlayer Film Materials (UL-1 to -12, Comparative UL-1 to -13)

In proportions shown in Table 2, compounds (A1) to (A8) and (R1) to (R8) described above were dissolved into a PGMEA solvent containing 0.1 mass % FC-4430 (manufactured by Sumitomo 3M Ltd.) optionally with a crosslinking agent (E1) as an additive and (S1) 1,6-diacetoxyhexane (boiling point: 260° C.) or (S2) tripropylene glycol monomethyl ether (boiling point: 242° C.) as high-boiling-point solvents. The solutions were filtered through a 0.1-μm filter made of a fluorinated resin. Thus, resist underlayer film materials (UL-1 to -12, Comparative UL-1 to -13) were prepared.

TABLE 2

| Resist underlayer film material | Polymer (parts by mass) | Crosslinking agent (parts by mass) | Solvent (parts by mass) | High-boiling-point solvent (parts by mass) |
|---|---|---|---|---|
| UL-1 | A1(100) | — | PGMEA (900) | — |
| UL-2 | A2(100) | — | PGMEA (900) | — |
| UL-3 | A3(100) | — | PGMEA (900) | — |
| UL-4 | A4(100) | — | PGMEA (900) | — |
| UL-5 | A5(100) | — | PGMEA (900) | — |
| UL-6 | A6(100) | — | PGMEA (900) | — |
| UL-7 | A7(100) | — | PGMEA (900) | — |
| UL-8 | A8(100) | — | PGMEA (900) | — |
| UL-9 | A2(100) | E1(20) | PGMEA (900) | — |
| UL-10 | A4(100) | — | PGMEA (800) | S1(100) |
| UL-11 | A6(100) | — | PGMEA (800) | S2(100) |
| UL-12 | A8(100) | E1(20) | PGMEA (800) | S2(100) |
| Comparative UL-1 | R1(100) | — | PGMEA (900) | — |
| Comparative UL-2 | R2(100) | — | PGMEA (900) | — |
| Comparative UL-3 | R3(100) | — | PGMEA (900) | — |
| Comparative UL-4 | R4(100) | — | PGMEA (900) | — |

TABLE 2-continued

| Resist underlayer film material | Polymer (parts by mass) | Crosslinking agent (parts by mass) | Solvent (parts by mass) | High-boiling-point solvent (parts by mass) |
|---|---|---|---|---|
| Comparative UL-5 | R5(100) | — | PGMEA (900) | — |
| Comparative UL-6 | R6(100) | — | PGMEA (900) | — |
| Comparative UL-7 | R7(100) | — | PGMEA (900) | — |
| Comparative UL-8 | R8(100) | — | PGMEA (900) | — |
| Comparative UL-9 | R4(100) | E1(20) | PGMEA (900) | — |
| Comparative UL-10 | R5(100) | E1(20) | PGMEA (900) | — |
| Comparative UL-11 | R6(100) | E1(20) | PGMEA (900) | — |
| Comparative UL-12 | R7(100) | E1(20) | PGMEA (900) | — |
| Comparative UL-13 | R8(100) | E1(20) | PGMEA (900) | — |

PGMEA: propylene glycol monomethyl ether acetate

The crosslinking agent (E1) is shown below.

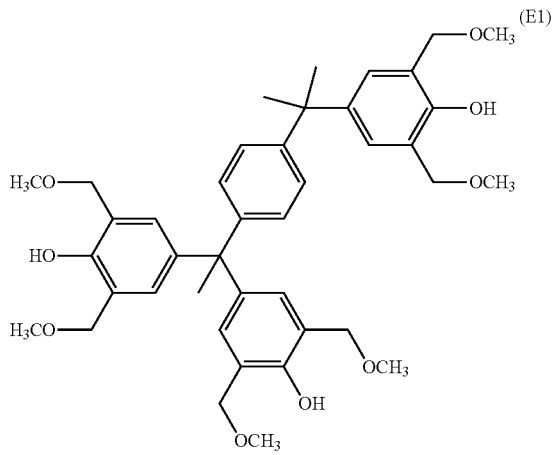 [SMILES: COCc1cc(C(C)(C)c2ccc(C(C)(c3cc(COC)c(O)c(COC)c3)c3cc(COC)c(O)c(COC)c3)cc2)cc(COC)c1O]

Solvent Resistance Evaluation (Examples 1-1 to 1-12, Comparative Examples 1-1 to 1-13)

The resist underlayer film materials (UL-1 to -12, Comparative UL-1 to -13) prepared above were each applied onto a silicon substrate, and baked at 250° C. for 60 seconds. After the film thickness was measured, a PGMEA solvent was dispensed on the film and allowed to stand. The resultant was spin dried for 30 seconds and baked at 100° C. for 60 seconds to evaporate the PGMEA solvent. The film thickness was measured again to evaluate the solvent resistance based on film thickness difference between before and after the PGMEA treatment. The following table shows the results.

TABLE 3

| | Resist underlayer film material | Film thickness after film formation: a(Å) | Film thickness after solvent treatment: b(Å) | b/a × 100(%) |
|---|---|---|---|---|
| Example 1-1 | UL-1 | 2012 | 2007 | 99.8 |
| Example 1-2 | UL-2 | 2009 | 2007 | 99.9 |
| Example 1-3 | UL-3 | 2007 | 2005 | 99.9 |
| Example 1-4 | UL-4 | 2010 | 2007 | 99.9 |
| Example 1-5 | UL-5 | 2014 | 2011 | 99.9 |
| Example 1-6 | UL-6 | 2015 | 2011 | 99.8 |
| Example 1-7 | UL-7 | 2020 | 2015 | 99.8 |
| Example 1-8 | UL-8 | 2008 | 2003 | 99.8 |
| Example 1-9 | UL-9 | 2023 | 2021 | 99.9 |
| Example 1-10 | UL-10 | 2021 | 2019 | 99.9 |
| Example 1-11 | UL-11 | 2022 | 2019 | 99.9 |
| Example 1-12 | UL-12 | 2018 | 2016 | 99.9 |
| Comparative Example 1-1 | Comparative UL-1 | 2003 | 1997 | 99.7 |
| Comparative Example 1-2 | Comparative UL-2 | 2011 | 2007 | 99.8 |
| Comparative Example 1-3 | Comparative UL-3 | 2009 | 2003 | 99.7 |
| Comparative Example 1-4 | Comparative UL-4 | 2004 | 24 | 1.2 |
| Comparative Example 1-5 | Comparative UL-5 | 2009 | 44 | 2.2 |
| Comparative Example 1-6 | Comparative UL-6 | 2004 | 48 | 2.4 |
| Comparative Example 1-7 | Comparative UL-7 | 2013 | 32 | 1.6 |
| Comparative Example 1-8 | Comparative UL-8 | 2003 | 32 | 1.6 |
| Comparative Example 1-9 | Comparative UL-9 | 2008 | 2002 | 99.7 |
| Comparative Example 1-10 | Comparative UL-10 | 2005 | 1997 | 99.6 |
| Comparative Example 1-11 | Comparative UL-11 | 2010 | 2006 | 99.8 |
| Comparative Example 1-12 | Comparative UL-12 | 2010 | 2006 | 99.8 |
| Comparative Example 1-13 | Comparative UL-13 | 2014 | 2008 | 99.7 |

As shown by Examples 1-1 to 1-12 in Table 3, when the inventive compounds were used, reduction in the film thickness by the solvent treatment was hardly observed. It can be seen that all the resist underlayer film materials resulted in films having favorable solvent resistance. This revealed that when the film is spin-coated with a silicon-containing resist middle layer film immediately thereabove, a laminate film can be formed without causing intermixing. In contrast, in Comparative Examples 1-4 to 1-8, in which no crosslinking agent was added, the film remaining ratios were less than 5% after the PGMEA treatment, and solvent resistance was not exhibited. To exhibit sufficient solvent resistance, adding a crosslinking agent was required as demonstrated in Comparative Examples 1-9 to 1-13.

Film Formability Evaluation (Examples 2-1 to 2-12, Comparative Examples 2-1 to 2-8)

The resist underlayer film materials (UL-1 to -12, Comparative UL-1 to -3, -9 to -13) prepared above were each applied onto a silicon substrate, and baked at 250° C. for 60 seconds to form a resist underlayer film having a film thickness of 100 nm. The states of the underlayer films thus formed were evaluated. The following table shows the results. Note that, in this evaluation to evaluate the coating property, thin films were formed. This is a strict evaluation condition because repelling is likely to occur.

TABLE 4

| | Composition | Film formability |
|---|---|---|
| Example 2-1 | UL-1 | no film formation failure |
| Example 2-2 | UL-2 | no film formation failure |
| Example 2-3 | UL-3 | no film formation failure |
| Example 2-4 | UL-4 | no film formation failure |
| Example 2-5 | UL-5 | no film formation failure |
| Example 2-6 | UL-6 | no film formation failure |
| Example 2-7 | UL-7 | no film formation failure |
| Example 2-8 | UL-8 | no film formation failure |
| Example 2-9 | UL-9 | no film formation failure |
| Example 2-10 | UL-10 | no film formation failure |
| Example 2-11 | UL-11 | no film formation failure |
| Example 2-12 | UL-12 | no film formation failure |
| Comparative Example 2-1 | Comparative UL-1 | film formation failure due to repellence |
| Comparative Example 2-2 | Comparative UL-2 | film formation failure due to repellence |
| Comparative Example 2-3 | Comparative UL-3 | film formation failure due to repellence |
| Comparative Example 2-4 | Comparative UL-9 | film formation failure due to repellence |
| Comparative Example 2-5 | Comparative UL-10 | no film formation failure |
| Comparative Example 2-6 | Comparative UL-11 | no film formation failure |
| Comparative Example 2-7 | Comparative UL-12 | film formation failure due to repellence |
| Comparative Example 2-8 | Comparative UL-13 | film formation failure due to repellence |

As shown by Examples 2-1 to 2-12 in Table 4, when the inventive compounds were used, all the resist underlayer film materials had favorable film formability (mirror surface state), and successfully formed films without any film-formation failure due to repellence. In contrast, as shown by Comparative Examples 2-1 to 2-4, 2-7, and 2-8, the resist underlayer films having no amide structure in the compounds were repelled on the silicon substrates, and favorable films were not formed. This suggests that having an amide structure in the compound increased the affinity between the resist underlayer film and the silicon substrate. Meanwhile, in Comparative Examples 2-2, 2-3, and 2-8, despite the similar scaffold structures, but films were not successfully formed. This suggests that having an amide structure at a structural terminal of the compound contributes to enhancement of the affinity between the resist underlayer film and the silicon substrate. Incidentally, no coating failure occurred in Comparative Examples 2-5 and 2-6 because the compounds had amide structures at the structural terminals.

Filling Property Evaluation (Examples 3-1 to 3-12, Comparative Examples 3-1 to 3-8)

The resist underlayer film materials (UL-1 to -12, Comparative UL-1 to -3, -9 to -13) prepared above were each applied onto a $SiO_2$ wafer substrate having a dense hole pattern (hole diameter: 0.16 μm, hole depth: 0.50 μm, distance between the centers of two adjacent holes: 0.32 μm) and baked at 250° C. for 60 seconds. Thus, resist underlayer films were formed. The substrate used was a base substrate 7 ($SiO_2$ wafer substrate) having a dense hole pattern as shown in FIG. 2 (G) (top view) and FIG. 2 (H) (sectional view). The sectional shapes of the resulting wafer substrates were observed with a scanning electron microscope (SEM) to check whether or not the holes were filled with the resist underlayer film 8 without voids (space). The following table shows the results. If a resist underlayer film material having poor filling property is used in this evaluation, voids occur inside the holes. When a resist underlayer film material having favorable filling property is used in this evaluation, the holes are filled with the resist underlayer film without voids as shown in FIG. 2 (I).

TABLE 5

| | Composition | Presence/absence of voids |
|---|---|---|
| Example 3-1 | UL-1 | absent |
| Example 3-2 | UL-2 | absent |
| Example 3-3 | UL-3 | absent |
| Example 3-4 | UL-4 | absent |
| Example 3-5 | UL-5 | absent |
| Example 3-6 | UL-6 | absent |
| Example 3-7 | UL-7 | absent |
| Example 3-8 | UL-8 | absent |
| Example 3-9 | UL-9 | absent |
| Example 3-10 | UL-10 | absent |
| Example 3-11 | UL-11 | absent |
| Example 3-12 | UL-12 | absent |
| Comparative Example 3-1 | Comparative UL-1 | absent |
| Comparative Example 3-2 | Comparative UL-2 | absent |
| Comparative Example 3-3 | Comparative UL-3 | absent |
| Comparative Example 3-4 | Comparative UL-9 | absent |
| Comparative Example 3-5 | Comparative UL-10 | absent |
| Comparative Example 3-6 | Comparative UL-11 | absent |
| Comparative Example 3-7 | Comparative UL-12 | present |
| Comparative Example 3-8 | Comparative UL-13 | absent |

As shown by Examples 3-1 to 3-12 in Table 5, when the inventive compounds were used, it was possible to fill the hole patterns without voids. This revealed that all the resist underlayer film materials were excellent in filling property. Meanwhile, in Comparative Example 3-7, voids were observed due to insufficient filling property.

Planarizing Property Evaluation (Examples 4-1 to 4-12, Comparative Examples 4-1 to 4-8)

The resist underlayer film materials (UL-1 to -12, Comparative UL-1 to -3, -9 to -13) prepared above were each applied onto a base substrate 9 ($SiO_2$ wafer substrate) having a giant isolated trench pattern (FIG. 3 (J), trench width: 10 μm, trench depth: 0.1 μm) and baked at 250° C. for 60 seconds. Then, a step (delta 10 in FIG. 3 (K)) between the trench portion and the non-trench portion of a resist underlayer film 10 was observed with an atomic force microscope (AFM) NX10 manufactured by Park systems Corp. The following table shows the results. In this evaluation, the smaller the step, the better the planarizing property. Note that, in this evaluation, a trench pattern having a depth of 0.10 μm was generally planarized using an organic film material having a film thickness of approximately 0.2 μm. This is a strict evaluation condition to evaluate the planarizing property.

TABLE 6

| | Composition | Step (nm) |
|---|---|---|
| Example 4-1 | UL-1 | 20 |
| Example 4-2 | UL-2 | 15 |
| Example 4-3 | UL-3 | 20 |
| Example 4-4 | UL-4 | 20 |
| Example 4-5 | UL-5 | 15 |
| Example 4-6 | UL-6 | 20 |
| Example 4-7 | UL-7 | 25 |
| Example 4-8 | UL-8 | 20 |
| Example 4-9 | UL-9 | 15 |
| Example 4-10 | UL-10 | 10 |
| Example 4-11 | UL-11 | 15 |
| Example 4-12 | UL-12 | 10 |
| Comparative Example 4-1 | Comparative UL-1 | 35 |
| Comparative Example 4-2 | Comparative UL-2 | 25 |
| Comparative Example 4-3 | Comparative UL-3 | 30 |
| Comparative Example 4-4 | Comparative UL-9 | 90 |
| Comparative Example 4-5 | Comparative UL-10 | 85 |
| Comparative Example 4-6 | Comparative UL-11 | 85 |
| Comparative Example 4-7 | Comparative UL-12 | 95 |
| Comparative Example 4-8 | Comparative UL-13 | 90 |

As shown by Examples 4-1 to 4-12 in Table 6, when the inventive compounds were used, the resist underlayer films had smaller steps between the trench portion and the non-trench portion compared with Comparative Examples 4-4 to 4-8. This revealed that the planarizing property was excellent. In Comparative Examples 4-1 to 4-3, relatively favorable planarizing property was exhibited, whereas more excellent planarizing property was exhibited in Examples 4-5, 4-6, and 4-8, which had the same scaffolds but contained the partial structures of the present invention. This also indicates the superiority of attaining higher flowability and enhanced affinity to the substrate to be processed as a result of incorporating the partial structures of the present invention. Moreover, it can be seen that planarizing property was further improved by adding the high-boiling-point solvent by comparison between Examples 4-10 to 4-12, where the high-boiling-point solvent was added, and Example 4-4, 4-6, 4-8, where the high-boiling-point solvent was not added.

Patterning Test (Examples 5-1 to 5-12, Comparative Examples 5-1 to 5-8)

The resist underlayer film materials (UL-1 to -12, Comparative UL-1 to -3, -9 to -13) prepared above were each applied onto a SiO$_2$ wafer substrate having a trench pattern (trench width: 10 μm, trench depth: 0.10 μm). Then, a resist underlayer film was formed by baking in the atmosphere at 250° C. for 60 seconds, so that the film thickness on the Bare-Si substrate was 200 nm. A silicon-containing resist middle layer material (SOG-1) was applied onto the resist underlayer film and baked at 220° C. for 60 seconds to form a resist middle layer film having a film thickness of 35 nm. A resist upper layer film material (SL resist for ArF) was applied thereon and baked at 105° C. for 60 seconds to form a resist upper layer film having a film thickness of 100 nm. A liquid immersion top coat material (TC-1) was applied onto the resist upper layer film and baked at 90° C. for 60 seconds to form a top coat having a film thickness of 50 nm.

The resist upper layer film material (monolayer resist for ArF) was prepared by: dissolving a polymer (RP1), an acid generator (PAG1), and a basic compound (Amine1) into a solvent containing 0.1 mass % FC-430 (manufactured by Sumitomo 3M Ltd.) in proportions shown in Table 7; and filtering the solution through a 0.1-μm filter made of a fluorinated resin.

TABLE 7

| | Polymer (parts by mass) | Acid generator (parts by mass) | Basic compound (parts by mass) | Solvent (parts by mass) |
|---|---|---|---|---|
| SL resist for ArF | RP1 (100) | PAG1 (6.6) | Amine1 (0.8) | PGMEA (2500) |

The structural formulae of the polymer (RP1), acid generator (PAG1), and basic compound (Amine1) used are shown below.

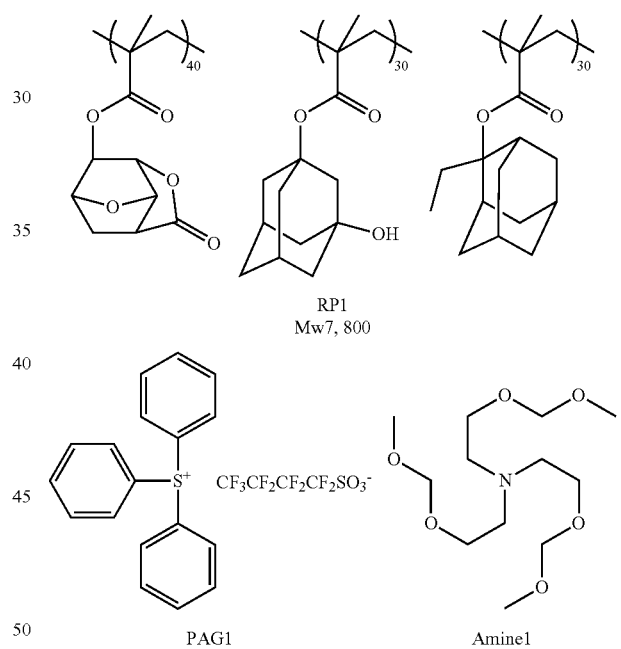

The liquid immersion top coat material (TC-1) was prepared by: dissolving a top coat polymer (PP1) into organic solvents in proportions shown in Table 8; and filtering the solution through a 0.1-μm filter made of a fluorinated resin.

TABLE 8

| Polymer (parts by mass) | Organic solvent (parts by mass) |
|---|---|
| TC-1 | PP1 (100) | diisoamyl ether (2700) 2-methyl-1-butanol (270) |

The structural formula of the polymer (PP1) used is shown below.

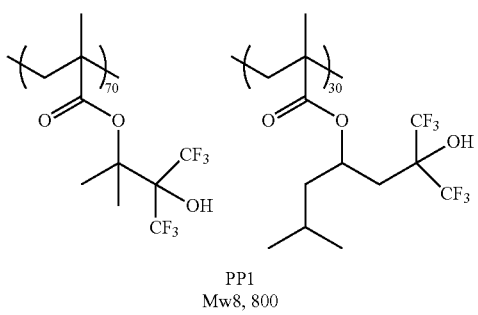

PP1
Mw 8,800

The silicon-containing resist middle layer material (SOG-1) was prepared by: dissolving a polymer represented by an ArF silicon-containing middle layer film polymer (SiP1) and a crosslinking catalyst (CAT1) into an organic solvent containing 0.1 mass % FC-4430 (manufactured by Sumitomo 3M Ltd.) in proportions shown in Table 9; and filtering the solution through a filter with a pore size of 0.1 μm made of a fluorinated resin.

TABLE 9

| Polymer (parts by mass) | Thermally crosslinking catalyst (parts by mass) | Organic solvent (parts by mass) |
|---|---|---|
| SOG-1 | SiP1 (100) | CAT1 (1) | propylene glycol monoethyl ether (4000) |

The structural formulae of the ArF silicon-containing middle layer film polymer (SiP1) and crosslinking catalyst (CAT1) used are shown below.

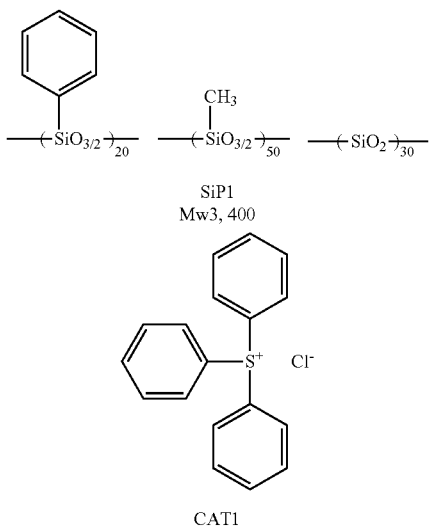

SiP1
Mw 3,400

CAT1

Next, the resulting substrate was exposed to light with an ArF liquid immersion exposure apparatus (NSR-S610C manufactured by Nikon Corporation, NA: 1.30, σ: 0.98/0.65, 35° s-polarized dipole illumination, 6% halftone phase shift mask), baked (PEB) at 100° C. for 60 seconds, and developed with a 2.38 mass % tetramethylammonium hydroxide (TMAH) aqueous solution for 30 seconds. Thus, a 55 nm 1:1 positive line and space pattern was obtained.

Next, using an etching apparatus Telius manufactured by Tokyo Electron Limited, the silicon-containing middle layer was processed by dry etching while using the resist pattern as a mask; the underlayer film was processed while using the silicon-containing middle layer as a mask; and the $SiO_2$ film was processed while using the underlayer film pattern as a mask. The etching conditions were as follows.

Conditions for transferring the resist pattern to the SOG film.
Chamber pressure: 10.0 Pa
RF power: 1,500 W
$CF_4$ gas flow rate: 15 sccm
$O_2$ gas flow rate: 75 sccm
Time: 15 sec Conditions for transferring the SOG pattern to the underlayer film.
Chamber pressure: 2.0 Pa
RF power: 500 W
Ar gas flow rate: 75 sccm
$O_2$ gas flow rate: 45 sccm
Time: 120 sec Conditions for transferring the organic film pattern to the $SiO_2$ film.
Chamber pressure: 2.0 Pa
RF power: 2,200 W
$C_5F_{12}$ gas flow rate: 20 sccm
$C_2F_6$ gas flow rate: 10 sccm
Ar gas flow rate: 300 sccm
$O_2$ gas flow rate: 60 sccm
Time: 90 sec The pattern cross sections were observed with an electron microscope (S-4700) manufactured by Hitachi, Ltd. Table 10 shows the results.

TABLE 10

| | Composition | Pattern profile after etching for transferring to substrate |
|---|---|---|
| Example 5-1 | UL-1 | vertical profile |
| Example 5-2 | UL-2 | vertical profile |
| Example 5-3 | UL-3 | vertical profile |
| Example 5-4 | UL-4 | vertical profile |
| Example 5-5 | UL-5 | vertical profile |
| Example 5-6 | UL-6 | vertical profile |
| Example 5-7 | UL-7 | vertical profile |
| Example 5-8 | UL-8 | vertical profile |
| Example 5-9 | UL-9 | vertical profile |
| Example 5-10 | UL-10 | vertical profile |
| Example 5-11 | UL-11 | vertical profile |
| Example 5-12 | UL-12 | vertical profile |
| Comparative Example 5-1 | Comparative UL-1 | pattern collapse |
| Comparative Example 5-2 | Comparative UL-2 | pattern collapse |
| Comparative Example 5-3 | Comparative UL-3 | pattern collapse |
| Comparative Example 5-4 | Comparative UL-9 | pattern collapse |
| Comparative Example 5-5 | Comparative UL-10 | pattern collapse |
| Comparative Example 5-6 | Comparative UL-11 | pattern collapse |
| Comparative Example 5-7 | Comparative UL-12 | pattern collapse |
| Comparative Example 5-8 | Comparative UL-13 | pattern collapse |

As shown by Examples 5-1 to 5-12 in Table 10, when the inventive compounds were used, the resist upper layer film patterns were favorably transferred to the final substrate in all the cases. This confirmed that the inventive materials for forming an organic film are suitably used in fine processing according to the multilayer resist method. On the other hand, in Comparative Examples 5-1 to 5-3, pattern collapse occurred locally because of the film-formation failure due to repellence as demonstrated in Comparative Examples 2-1 to 2-3. Meanwhile, in Comparative Examples 5-4 to 5-8, pattern collapse occurred at the patterning and it was impossible to form a pattern because of poor planarizing property as demonstrated in Comparative Examples 4-4 to 4-8.

From the above, it was revealed that the inventive resist underlayer film materials have favorable coating property and high filling and planarizing properties. Thus, the inventive resist underlayer film materials are quite useful as underlayer film materials used in multilayer resist methods. Moreover, the inventive patterning processes using the materials can form a fine pattern with high precision even when the body to be processed is a stepped substrate.

It should be noted that the present invention is not limited to the above-described embodiments. The embodiments are just examples, and any examples that substantially have the same feature and demonstrate the same functions and effects as those in the technical concept disclosed in claims of the present invention are included in the technical scope of the present invention.

The invention claimed is:

1. A resist underlayer film material used in a multilayer resist method, comprising:
   (A) at least one compound shown by the following general formula (1); and
   (B) an organic solvent,

(1)

wherein X independently represents a monovalent organic group shown by the following general formula (2); W represents an organic group with a valency of "n" having 2 to 60 carbon atoms, and containing an "m" number of partial structures each independently shown by the following general formula (4) or (5); and "m" and "n" each represent an integer of 1 to 10,

(2)

wherein a broken line represents a bonding arm; Z represents an aromatic group with a valency of (k+1) having 6 to 20 carbon atoms; A represents a single bond or —O—(CH$_2$)$_p$—; "k" represents an integer of 1 to 5; and "p" represents an integer of 1 to 10,

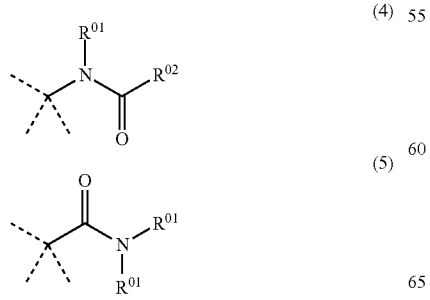
(4)

(5)

wherein broken lines represent bonding arms; $R^{01}$ represents a hydrogen atom or a monovalent alkyl group having 1 to 10 carbon atoms; and $R^{02}$ represents a hydrogen atom or a monovalent alkyl group having 1 to 20 carbo atoms.

2. The resist underlayer film material according to claim 1, wherein A in the general formula (2) is —OCH$_2$—.

3. The resist underlayer film material according to claim 1, wherein W in the general formula (1) is represented by any of the following general formulae (6-1) to (6-5),

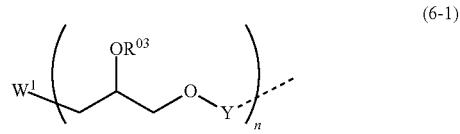
(6-1)

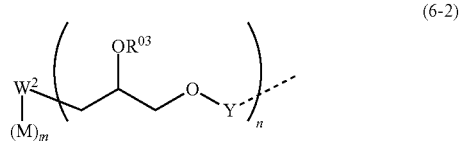
(6-2)

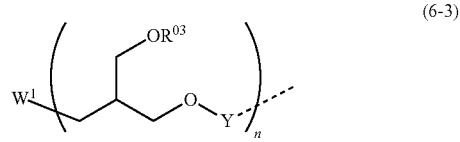
(6-3)

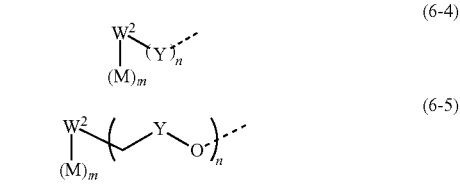
(6-4)

(6-5)

wherein broken lines represent bonding arms; $R^{03}$ represents any of a hydrogen atom, an alkyl group or acyl group having 1 to 20 carbon atoms optionally containing an oxygen atom or nitrogen atom, and the structure of the general formula (3); M represents an organic group containing the structure of the general formula (3); $W^1$ represents an organic group with a valency of "n" having 1 to 57 carbon atoms; $W^2$ represents an organic group with a valency of (m+n); Y represents a single bond or a carbonyl group; and "m" and "n" each represent an integer of 1 to 10.

4. The resist underlayer film material according to claim 3, wherein $W^1$ or $W^2$ in the general formulae (6-1) to (6-5) comprises a structure shown by any of the following formulae:

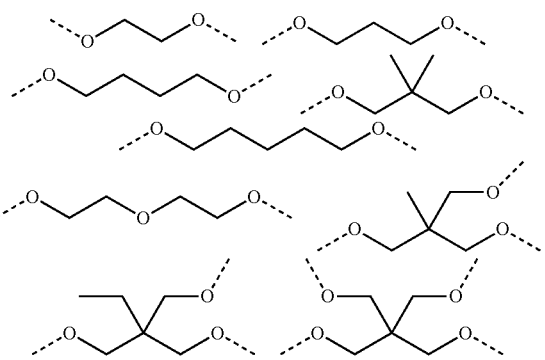

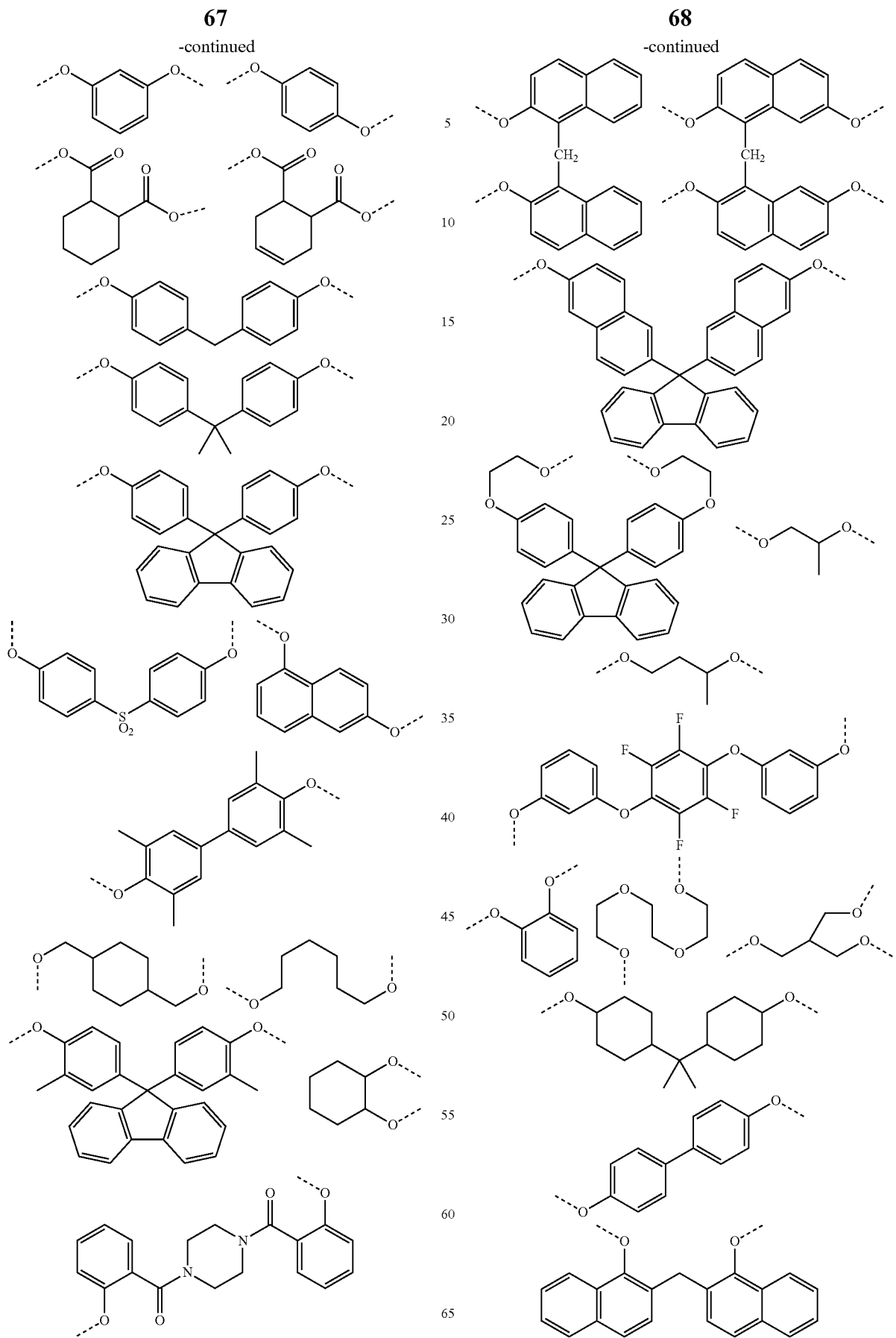

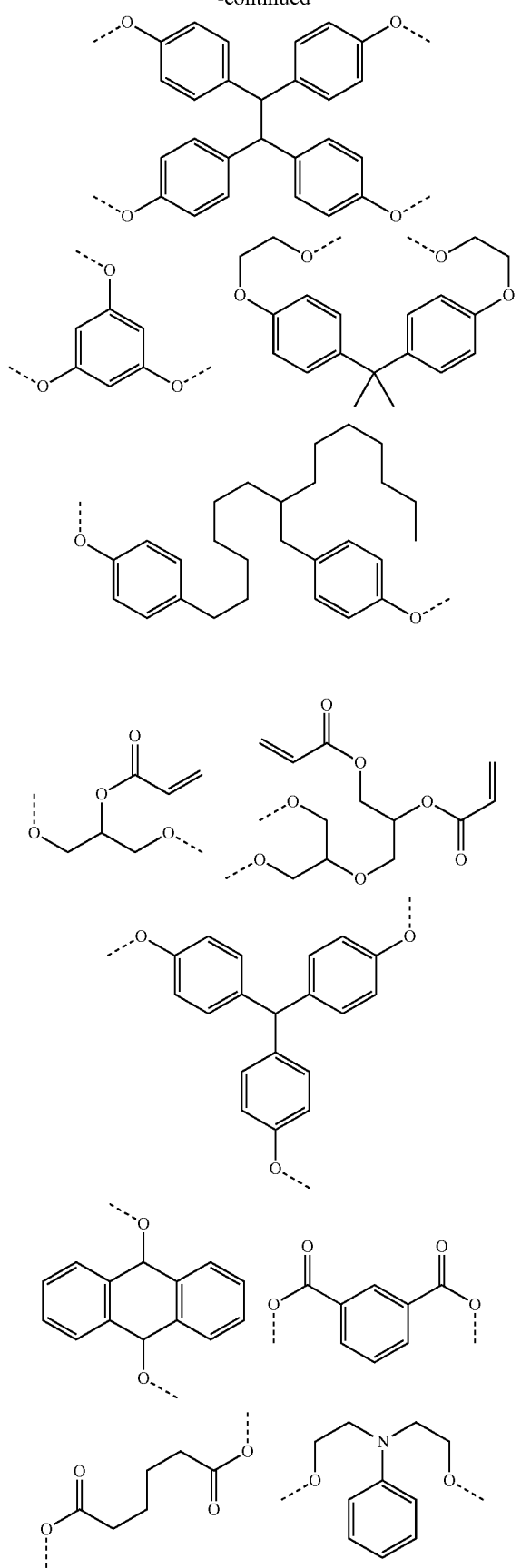
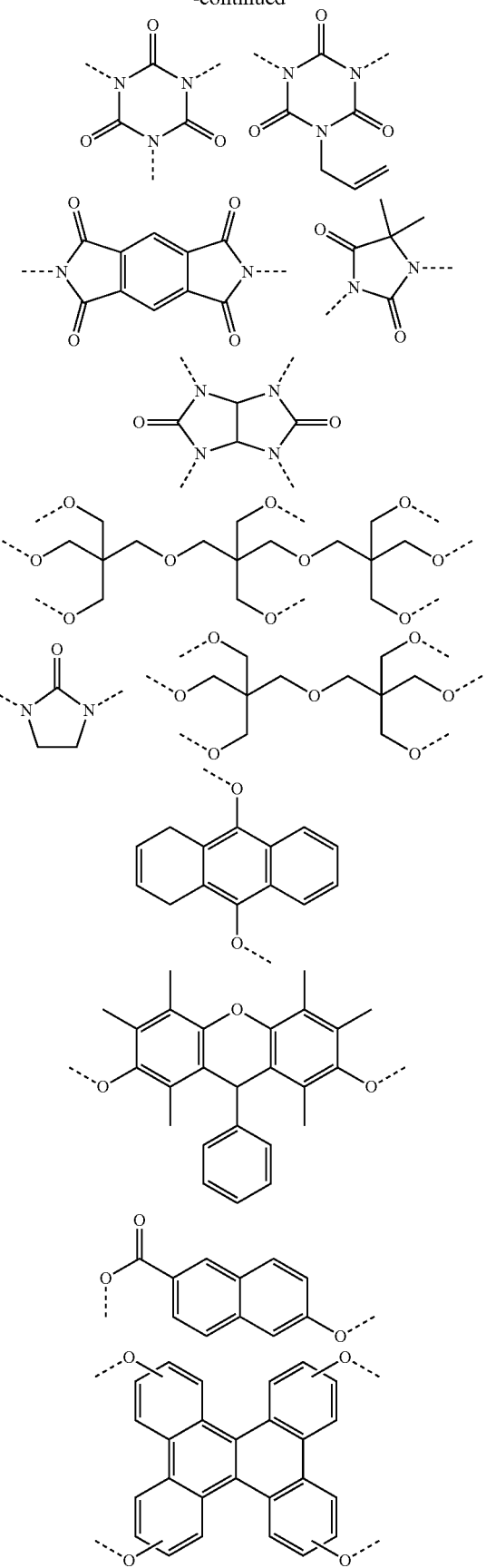

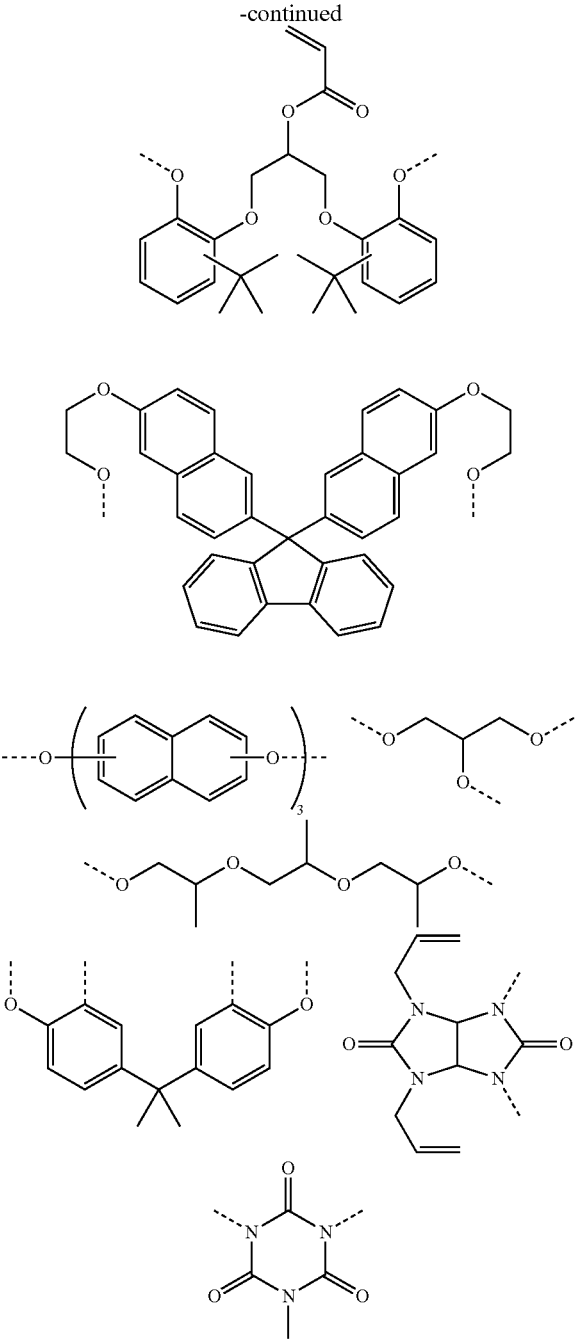

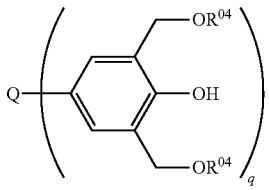

wherein Q represents a single bond, or a hydrocarbon group with a valency of "q" having 1 to 20 carbon atoms; $R^{04}$ represents a hydrogen atom, or an alkyl group having 1 to 20 carbon atoms; and "q" represents an integer of 1 to 5.

8. A patterning process for forming a pattern in a substrate to be processed, comprising steps of:
(I-1) applying the resist underlayer film material according to claim 1 onto a substrate to be processed, followed by heating to form a resist underlayer film;
(I-2) forming a resist upper layer film on the resist underlayer film by using a photoresist material;
(I-3) subjecting the resist upper layer film to pattern exposure and then development with a developer to form a pattern in the resist upper layer film;
(I-4) transferring the pattern to the resist underlayer film by dry etching while using the resist upper layer film having the formed pattern as a mask; and
(I-5) processing the substrate to be processed while using the resist underlayer film having the formed pattern as a mask to form the pattern in the substrate to be processed.

9. The patterning process according to claim 8, wherein the substrate to be processed has a structure or step with a height of 30 nm or more.

10. A patterning process for forming a pattern in a substrate to be processed, comprising steps of:
(II-1) applying the resist underlayer film material according to claim 1 onto a substrate to be processed, followed by heating to form a resist underlayer film;
(II-2) forming a resist middle layer film on the resist underlayer film;
(II-3) forming a resist upper layer film on the resist middle layer film by using a photoresist material;
(II-4) subjecting the resist upper layer film to pattern exposure and then development with a developer to form a pattern in the resist upper layer film;
(II-5) transferring the pattern to the resist middle layer film by dry etching while using the resist upper layer film having the formed pattern as a mask;
(II-6) transferring the pattern to the resist underlayer film by dry etching while using the resist middle layer film having the transferred pattern as a mask; and
(II-7) processing the substrate to be processed while using the resist underlayer film having the formed pattern as a mask to form the pattern in the substrate to be processed.

11. The patterning process according to claim 10, wherein the substrate to be processed has a structure or step with a height of 30 nm or more.

12. A patterning process for forming a pattern in a substrate to be processed, comprising steps of:
(III-1) applying the resist underlayer film material according to claim 1 onto a substrate to be processed, followed by heating to form a resist underlayer film;

wherein broken lines represent bonding arms.

5. The resist underlayer film material according to claim 1, wherein the organic solvent (B) is a mixture of one or more organic solvents each having a boiling point of lower than 180° C. and one or more organic solvents each having a boiling point of 180° C. or higher.

6. The resist underlayer film material according to claim 1, further comprising one or more of (C) an acid generator, (D) a surfactant, (E) a crosslinking agent, (F) a plasticizer, and (G) a pigment.

7. The resist underlayer film material according to claim 6, comprising at least one compound shown by the following general formula (7) as the crosslinking agent (E), (III-2) forming an inorganic hard mask middle layer film selected from a silicon oxide film, a silicon nitride film, and a silicon oxynitride film on the resist underlayer film;

(III-3) forming an organic thin film on the inorganic hard mask middle layer film;

(III-4) forming a resist upper layer film on the organic thin film by using a photoresist material;

(III-5) subjecting the resist upper layer film to pattern exposure and then development with a developer to form a pattern in the resist upper layer film;

(III-6) transferring the pattern to the organic thin film and the inorganic hard mask middle layer film by dry etching while using the resist upper layer film having the formed pattern as a mask;

(III-7) transferring the pattern to the resist underlayer film by dry etching while using the inorganic hard mask middle layer film having the transferred pattern as a mask; and (III-8) processing the substrate to be processed while using the resist underlayer film having the formed pattern as a mask to form the pattern in the substrate to be processed.

13. The patterning process according to claim 12, wherein the substrate to be processed has a structure or step with a height of 30 nm or more.

14. A method for forming a resist underlayer film that serves as an organic planarizing film employed in a semiconductor device manufacturing process, the method comprising:

spin-coating a substrate to be processed with the resist underlayer film material according to claim 1; and heating the substrate coated with the resist underlayer film material at a temperature of 100° C. or higher and 600° C. or lower for 10 to 600 seconds to form a cured film.

15. The method for forming a resist underlayer film according to claim 14, wherein the substrate to be processed has a structure or step with a height of 30 nm or more.

16. A method for forming a resist underlayer film that serves as an organic planarizing film employed in a semiconductor device manufacturing process, the method comprising:

spin-coating a substrate to be processed with the resist underlayer film material according to claim 1; and heating the substrate coated with the resist underlayer film material under an atmosphere with an oxygen concentration of 1% or more and 21% or less to form a cured film.

17. The method for forming a resist underlayer film according to claim 16, wherein the substrate to be processed has a structure or step with a height of 30 nm or more.

18. A method for forming a resist underlayer film that serves as an organic planarizing film employed in a semiconductor device manufacturing process, the method comprising:

spin-coating a substrate to be processed with the resist underlayer film material according to claim 1; and heating the substrate coated with the resist underlayer film material under an atmosphere with an oxygen concentration of less than 1% to form a cured film.

19. The method for forming a resist underlayer film according to claim 18, wherein the substrate to be processed has a structure or step with a height of 30 nm or more.

* * * * *